United States Patent
Sclabassi et al.

(10) Patent No.: US 12,048,551 B2
(45) Date of Patent: Jul. 30, 2024

(54) MODULAR NeuroNet-VII INTRAOPERATIVE NEUROPHYSIOLOGICAL MONITORING SYSTEM

(71) Applicants: Robert Joseph Sclabassi, Gibsonia, PA (US); Yicheng Bai, Sewickley, PA (US); Rafael Eugenio Herrera, Pittsburgh, PA (US)

(72) Inventors: Robert Joseph Sclabassi, Gibsonia, PA (US); Yicheng Bai, Sewickley, PA (US); Rafael Eugenio Herrera, Pittsburgh, PA (US)

(73) Assignee: COMPUTATIONAL DIAGNOSTICS, INC, Pittsburgh, PA (US)

(*) Notice: Subject to any disclaimer, the term of this patent is extended or adjusted under 35 U.S.C. 154(b) by 0 days.

(21) Appl. No.: 17/901,376

(22) Filed: Sep. 1, 2022

(65) Prior Publication Data
US 2023/0329626 A1 Oct. 19, 2023

Related U.S. Application Data

(60) Provisional application No. 63/240,553, filed on Sep. 3, 2021.

(51) Int. Cl.
*A61B 5/383* (2021.01)
*A61B 5/378* (2021.01)
(Continued)

(52) U.S. Cl.
CPC ............. *A61B 5/383* (2021.01); *A61B 5/378* (2021.01); *A61B 5/38* (2021.01); *A61B 50/13* (2016.02); *A61B 90/20* (2016.02)

(58) Field of Classification Search
CPC ........... A61B 5/383; A61B 5/378; A61B 5/38; A61B 50/13; A61B 90/20
See application file for complete search history.

(56) References Cited

U.S. PATENT DOCUMENTS

| 6,334,068 B1 * | 12/2001 | Hacker | A61B 5/4893 600/545 |
| 2010/0001864 A1 | 1/2010 | O'Brien et al. | |

(Continued)

OTHER PUBLICATIONS

"NEURO-IOM (v. 2) Multimodal System for Intraoperative Neurophysiologic Monitoring" Jul. 2021, Neurosoft, 1-16 (Year: 2021).*
(Continued)

*Primary Examiner* — May A Abouelela
*Assistant Examiner* — Anna Roberts
(74) *Attorney, Agent, or Firm* — ACKER WOOD IP LAW, LLP; Gwen B. Acker Wood

(57) ABSTRACT

The invention provides an advanced, modular, intraoperative neurophysiological monitoring (IONM) system, referred to as a "NeuroNet-VII" System, which is the first IONM system designed with a USB hub architecture comprising serially-connected functional "pods which provides multi-modality simultaneous data acquisition which supports all data types useful in operating rooms, diagnostic laboratories, intensive care units, and epilepsy monitoring units. The unique pod architecture makes the IONM system highly modular compared to current systems which typically place components in a limited number of centralized enclosures. The modular architecture of the invention also provides for real-time collection of data so that information may be communicated with a remotely-located physician; a user needs only to purchase pods that are needed; repair of a single pod may easily be replaced without disabling the entire system; and advances in hardware designs may be implemented for a specific pod without requiring replacement of the entire system.

19 Claims, 26 Drawing Sheets
(20 of 26 Drawing Sheet(s) Filed in Color)

(51) Int. Cl.
    *A61B 5/38*     (2021.01)
    *A61B 50/13*    (2016.01)
    *A61B 90/20*    (2016.01)

(56) References Cited

U.S. PATENT DOCUMENTS

| | | |
|---|---|---|
| 2011/0028860 A1 | 2/2011 | Chenaux et al. |
| 2012/0004516 A1* | 1/2012 | Eng ............... A61B 5/0015 |
| | | 600/301 |
| 2014/0163411 A1 | 6/2014 | Rea |
| 2015/0032022 A1 | 1/2015 | Stone et al. |
| 2016/0038074 A1* | 2/2016 | Brown ............ A61M 16/0443 |
| | | 600/554 |
| 2018/0075199 A1* | 3/2018 | Meyerson ............ A61B 5/002 |
| 2018/0130325 A1 | 5/2018 | Kiani et al. |
| 2018/0168458 A1* | 6/2018 | Pekander ............ A61B 5/0809 |
| 2020/0015687 A1* | 1/2020 | Drakulic ............ A61B 5/7203 |
| 2020/0146573 A1* | 5/2020 | Rehfeldt ................ A61B 5/24 |
| 2021/0169721 A1* | 6/2021 | Huber .................. A61G 7/072 |
| 2022/0104822 A1* | 4/2022 | Shelton, IV .......... G16H 40/67 |
| 2022/0313369 A1* | 10/2022 | Oberkircher ......... A61B 34/37 |

OTHER PUBLICATIONS

"Neuromaster MEE-2000 Intra-operative monitoring system" Retrieved from Jul. 5, 2016 via Wayback Machine, Nihon Kohden, 1-6 (Year: 2016).*

* cited by examiner

MODULAR NeuroNet-VII INTRAOPERATIVE NEUROPHYSIOLOGICAL MONITORING SYSTEM

FIELD OF THE INVENTION

The present invention relates to intraoperative neurophysiological monitoring (IONM) systems and, in particular, to a modular IONM system that includes a conceptually unique system architecture comprising serial pods that allow for real-time collection of data and for software which allows for communications with a remote attending physician to allow this information to be used to significantly reduce patient morbidity.

BACKGROUND OF THE INVENTION

Intraoperative neurophysiological monitoring (IONM) utilizes a group of procedures based on neurophysiological measures including sensory evoked potentials, motor evoked potentials, electroencephalograms and electromyograms, used during surgical procedures, including, but not limited to high-risk neurosurgical, orthopedic, peripheral nerve, and vascular surgeries to monitor the functioning of the central and peripheral nervous system. These procedures assist surgeons in preventing damage to and preserving functionality of the nervous system.

Intraoperative neurophysiological monitoring is currently used in thousands of surgical procedures every year. The first use of IONM dates back to the 1930s, when direct stimulation of the brain was used to identify the motor cortex of patients with epilepsy undergoing intracranial surgery. Later on, it was the introduction of new monitoring techniques and commercial IONM machines in the early 1980s that allowed for the widespread adaptation of this technique.

Technological advances in the last twenty years have allowed monitoring techniques to continually evolve. The enhanced computational power and widespread availability of computer networks and communication systems has allowed IONM data to be acquired in greater and more relevant amounts and for the interpretation of this data to be performed from remote sites in real-time. This has made IONM more relevant and accessible in the last two decades.

Currently, however, available IONM systems present with several important drawbacks, namely: (1) placement of the system electronics in centralized enclosures rather than as distributed modular components limiting the flexibility and increasing the cost of these systems; (2) the use of blocking capacitors to remove DC drift, which has the undesired effect of removing very low signal frequencies; (3) inability to remove the electrical noise produced by the high frequencies and voltages used in electrocautery which prevents the IONM systems from acquiring data during the times when cautery is being used; (4) lack of a method to suppress excess common noise which obscures the signals of interest for extended periods of time; (5) a limited number of data channels not allowing all data of interest to be acquired; (6) a limited amount of data storage which limits the amount of acquired data which may be stored during a particular procedure; (7) limitations in the methods for presenting stimulation data; and (8) limitations in the methods for presenting data remotely and the bi-directional communication channels supporting the interpretation of these data. There is an important need, therefore, for an IONM system that not only addresses these shortcomings but improves the state of the art of IONM systems to an advanced level of functionality, versatility and performance.

SUMMARY OF THE INVENTION

The present invention fulfills this need by providing a unique intraoperative neurophysiological monitoring (IONM) system, referred to as "NeuroNet-VII" ("the NeuroNet-VII System" or "the System"), which is the first IONM system designed with a system architecture comprising serial modules. This conceptually unique architecture includes a number of novel features and utilizes novel engineering approaches to address and overcome the drawbacks enumerated above. The nature of the module architecture makes the system highly modular as opposed to all other prior art systems which tend to place all the components in a limited number of centralized enclosures.

The modular architecture of the present invention is of value to users for several reasons: (1) the user only needs to buy the modules that are needed; (2) a module in need of repair will not disable the entire system but may be easily individually replaced; and (3) advances in hardware designs may be implemented for a specific module without requiring replacement of an entire system.

The NeuroNet-VII system of the present invention utilizes distributed computer technology to meet four objectives: (1) the acquisition and processing of multi-modality data; (2) the integration of these data into various display formats suitable for specific applications; (3) the management of data communication between the serial modules; and (4) the presentation of the various data types in such a way as to allow multiple individuals at various distributed sites to consult in meaningful ways concerning the shared data as well as to interpret the shared data.

The NeuroNet-VII system provides several unique features: (1) true multi-modality simultaneous data acquisition supporting all data types useful in the operating room, diagnostic laboratories, intensive care unit and epilepsy monitoring unit; (2) extensive intra- and internet communication facilities supporting data, text, video and audio multi-directional distribution; (3) elegant graphical user interfaces providing ease of use and efficient data presentation; and (4) a set of signal processing and data analysis tools.

The NeuroNet-VII system acquires, processes and displays physiological data from selected areas of the central and peripheral nervous system essentially in a simultaneous fashion. This allows for real-time assessment of data, both locally and remotely, and for communications with a remote attending physician so that this information can be used to reduce morbidity.

The NeuroNet-VII system is designed to support intraoperative neurophysiological monitoring, intensive care unit (ICU) neurophysiological monitoring, neurophysiological diagnostic testing including electroencephalograms (EEGs), electromyograms (EMG)s (fine needle), evoked potentials (EPs) both sensory and motor, epilepsy evaluations including synchronized video acquisition and analysis in epilepsy monitoring units, and mobile monitoring while transporting a patient.

In one aspect of the invention, the System provides a modular, intraoperative neurophysiological monitoring system comprising a head module (Computational Module) and one or more serially connected functional modules, each of which contains a communications board (Neuron Board) which contains a USB hub and a field-programmable gate array (FPGA) processor. The serially connected functional modules comprise one or more Data Acquisition modules, an Electrical Stimulation module, and an Auditory/Visual Stimulation module. The serially connected functional modules may be serially connected in any order depending on the preference of the user for a particular procedure. The head module is either a Core computational module which is mounted on a cart, or a portable system utilizing a commercial laptop as the computational module. In either case, the head (or first) module also contains a base board. The base board also contains both a USB hub and an FPGA chip and facilitates data concatenation of all data types being collected.

In another aspect of the invention, the System provides a unique USB hub architecture, which provides power to all modules and allows for bidirectional communications between the modules and for system synchronization. This modified USB architecture provides up to seven cascading tiers of devices including the computational module and the base board comprising the first two devices.

In another aspect of the invention, the System provides a sensing circuit located in each module which senses which module is the seventh or in the last tier in a chain and provides that another module is not connected downstream so that no more than five functional modules are interconnected and that the fifth, or last functional module, is recognized as a device.

In another aspect of the invention, the System provides an electrocautery suppression filter, which is a front-end filter to eliminate high frequency and high voltage noise injected into the system by an electrocautery device. The electrocautery suppression filter allows for continual recording of essential neurological signals during the time that an electrocautery device is being used.

In another aspect of the invention, the System provides common mode noise suppression which utilizes feedback to a patient of the noise component of signals being measured, in which the feedback signal is capable of balancing out common mode noise.

In another aspect of the invention, the System provides DC drift correction by utilizing a reference pin of an instrumentation amplifier which biases the baseline of the output of the amplifier in order to cancel the DC drift from input.

In another aspect of the invention, the System provides organic light-emitting diode (OLED) indicators for module number identification and electrode identification by the use of a plurality of full color OLED screens. In an embodiment, there are three full color OLED screens.

In another aspect of the invention, the System provides A/D conversion which implements signal differencing after digitization in order to generate more data channels than prior art systems, and thus allows for additional ways to present data than previously implemented.

In another aspect of the invention, the System provides a stimulus artifact blanking and trace restore function which allows for data to be acquired without containing contaminating stimulus artifacts and for electrical stimulation to be applied adjacent to recording electrodes, which allows for signals to be recorded through these electrodes immediately after the completion of the stimulating pulses. The application of blanking signals is under the control of a local FPGA chip contained on the communications board.

In another aspect of the invention, the System comprises a plurality of electrical stimulators in the Electrical Stimulation module to produce a variety of train patterns for stimuli which may be synchronized to provide for apparent simultaneous acquisition of multi-modality electrical evoked potentials. The Electrical Stimulation module provides both constant current and constant voltage mode stimulation which can be used interchangeably for electrical stimulation, and which supports both uniphasic and biphasic electrical stimulation, all of which may be interchanged at a user's discretion. The control of these stimulus patterns is provided by the FPGA chip on the communications board. In an embodiment, the Electrical Stimulation module contains eight electrical stimulators.

In another aspect of the invention, the System comprises, in the Auditory/Visual Stimulation module, sound output to ear buds for auditory stimulation and visual output to either a video graphic array (VGA) monitor or to goggles for visual stimulation. Visual stimulation by the VGA monitor is driven through a VGA full color range encoder chip, where patterns are predefined with different color, texture, intensity, and flashing frequency. The full color range stimulation with variety patterns and frequencies makes the system capable of producing complicated visual-related evoked potential signal monitoring. Pattern visual stimulation may also be provided through the goggles. The control of the stimulus patterns is provided by the FPGA chip on the previously described communications board.

In another aspect of the invention, the System comprises a plurality of layers of electrical isolation for a patient in order to isolate the patient from an electrical current path from the patient to earth ground.

BRIEF DESCRIPTION OF DRAWINGS

The patent or application file contains at least one drawing executed in color. Copies of this patent or patent application publication with color drawing(s) will be provided by the Office upon request and payment of the necessary fee.

For the present disclosure to be easily understood and readily practiced, the present disclosure will now be described for purposes of illustration and not limitation in connection with the following figures, where like reference numerals refer to identical or functionally similar elements throughout the separate views.

DETAILED DESCRIPTION OF THE INVENTION

As used herein, the terms "computational module" and "compute model" are meant to be interchangeable.

As used herein, the terms "head module," "computational module," and "first module" are meant to be interchangeable.

As used herein, the terms "communications board" and "neuron board" are meant to be interchangeable.

As used herein, the terms "pod," "module," and "component" are meant to be interchangeable.

As used herein, the terms "serially connected functional pods," "tier," and "device" are meant to be interchangeable.

Illustrative embodiments of the invention are described below. In the interest of clarity, not all features of an actual implementation are described in this specification. It will of course be appreciated that in the development of any such actual embodiment, numerous implementation-specific decisions must be made to achieve the inventors' specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure. The systems disclosed herein boast a variety of inventive features and components that warrant patent protection, both individually and in combination.

Figure 1:
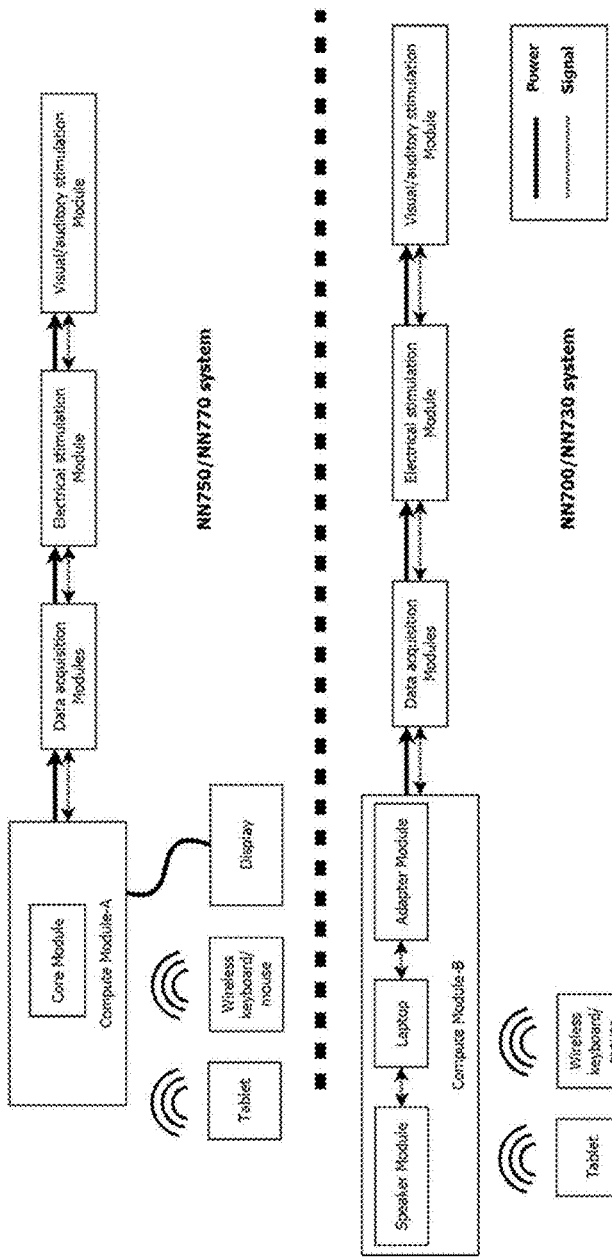
FIG. 1 shows the NeuroNet-VII system architecture, where the top panel is a NeuroNet-VII system with Computational Module A, containing a core device interface (CDI)-designed core module, and the lower panel is a NeuroNet-VII system with Computational Module B, containing a laptop computer, a CDI adapter module comprising a Base board and power supply, in accordance with an embodiment of the invention.

As shown in FIG. 1, the NeuroNet-VII system comprises two configurations: (1) a cart-based NeuroNet-VII configuration utilizing Compute Module A, which has a Core module as the computational unit, functional modules, and accessories such as display monitor, control tablet, and wireless input devices; and (2) a portable NeuroNet-VII configuration utilizing Compute Module B, which has a commercial PC, a Base Board as an interface between the PC and the downstream series of functional modules. Table 1 shows the difference between these two Compute Modules. Compute Module A (for the NN750/NN770 assemblies) contains a Core Module which include the CDI designed Core board (computational engine), a Base Board which is used as a multi-media data collection board, the CDI designed Speaker module and a medically certified power supply. Compute Module B (for the NN700/NN730 assemblies) consists of a laptop computer, an Adapter module which contains a Base Board and a medically certified power supply, and a Speaker module.

TABLE 1

NeuroNet-VII Compute Module Configurations

| Module name | Module types | Components packaging | Module components |
| --- | --- | --- | --- |
| Compute Module | Compute Module A (NN750/NN770) | Core module | Core board Base board Power supply Speaker |
| | Compute Module B (NN700/NN730) | Laptop Adapter module Speaker module | Laptop Base board Power supply Speaker |

The Compute Module fulfills four functions. (1) It contains a computational engine designed to function as the signal processing, computational center of the system, as well as having features for displaying and storing data. The Compute Module is always the head item in a chain of modules. (2) It provides for data communication to the downstream modules which either acquire data from a patient or provide stimuli to the patient. (3) It provides for the acquisition and integration of data from other devices, which includes, without limitation, anesthesia monitoring devices, imaging systems, and video from microscopes, endoscopes, or other cameras, and the injection of signals into the operating microscope. (4) It provides for connectivity to the internet either through ethernet or wireless connectivity. The Compute Module, in addition to use of a keyboard and display, may be controlled by a tablet connected by BLUETOOTH®. The tablet may also be used to display data.

The System of the present invention is the first intraoperative neurophysiological monitoring (IONM) system designed using modules which are serially connected, or daisy chained, together. The System includes three types of functional modules: (1) Data Acquisition Modules; (2) Electrical Stimulation Module; and (3) Auditory/Visual Stimulation Module. A Data Acquisition Module is designed to acquire data from a subject. The Electrical Stimulation Module and the Auditory/Visual Stimulation Module are designed to stimulate the subject to evoke signals from the subject's nervous system. The modules are designed to be interconnected in any order; i.e., any module may be first in a chain of modules. The System recognizes what the place of each module is in a chain of modules and assigns each module its correct identification. Whichever Data Acquisition Module is the initial acquisition module, has its electrodes assigned numbers 1 through 24 by the system. The second acquisition module's electrodes are assigned numbers 25 through 48 and the third acquisition module has its electrodes assigned the numbers 49 through 72. An acquisition module does not need to be the first module in a chain of modules and the data acquisition modules do not need to be adjacent to each other. As shown in FIG. 1, except for the Compute Module, the two System configurations may be identical.

Table 2 enumerates the electronic boards contained in the Compute Modules and in the Modules.

TABLE 2

Core and Pods Contained in the Electronic Boards

| Modules | Boards | Description |
| --- | --- | --- |
| Compute Module A | BN7-U003 | Base Board |
| | BN7-C001 | Core Board, Computer Processor/Storage |
| | BN7-C002 | Power Supply |
| | CN7-C114 | Speaker Assemble |
| | Tablet | Alternative method of Display Control Panel and Data from Core |
| Data Acquisition POD | BN7-A001 | Amplifiers/Filters and A/D |
| | BN7-A002 | Electrode Pin/Filer Board |
| | BN7-U001 | FPGA/USB Communication Board |
| | BN7-U002 | Display Board - Pin Identification |
| Electrical Stimulator POD | BN7-E001 | Electrical Stimulation Board |
| | BN7-E002 | Stimulator Pin Board |
| | BN7-P001 | Extender Pod Board |
| | BN7-U001 | FPGA/USB Communication Board |
| | BN7-U002 | OLED Display Board |
| Audio/Visual Stimulator POD | BN7-B001 | A/V Stimulation Board |
| | BN7-U001 | FPGA/USB Communication Board |
| | BN7-U002 | OLED Display Board |
| (Applied Part) | BN7-G001 | Left Eye Stimulation Goggle |
| (Applied Part) | BN7-G002 | Right Eye Stimulation Goggle |
| | BN7-B103 | Ear Buds |

TABLE 2-continued

Core and Pods Contained in the Electronic Boards

| Modules | Boards | Description |
| --- | --- | --- |
| Compute Module B | Laptop Computer | Standard computer. |
| | BN7-U003 | Base Board (Interface unit between pods and laptop) |

Figure 2:
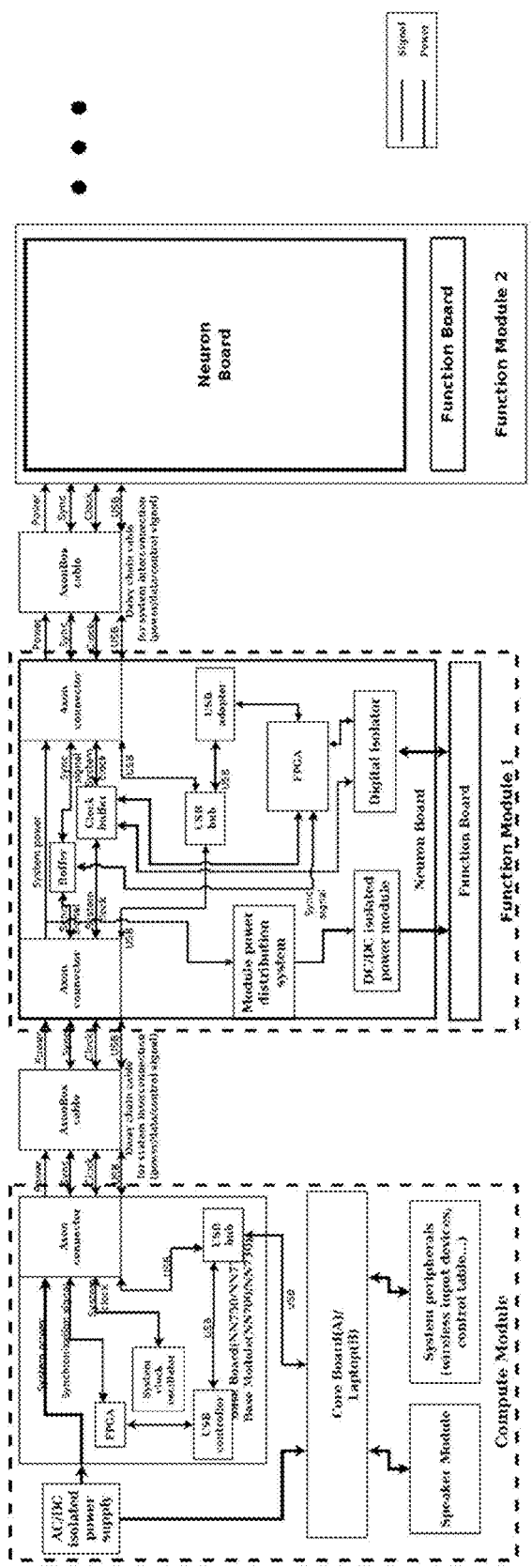
FIG. 2 is a schematic of the Detailed System Architecture, showing the module interconnection scheme, with red lines indicating power distribution and blue lines information distribution, in accordance with an embodiment of the invention.

FIG. 2 illustrates the overall module interconnection scheme with red lines indicating power distribution and the blue line indicating information distribution, which shall be described in detail below.

Interconnection Between Modules

The interconnection between the modules is based on a CDI developed architecture, the Axon Architecture which provides power to all the modules, system synchronization between all the modules and which utilizes USB bidirectional communications facilities. Each module is uniquely identifiable as to its type and sequence in the series. Each functional module contains a Neuron Communication board (BN7-U001) which provides the hardware implementation of the functions described in this section. Due to the unique nature of the Axon network architecture, there may be as many as thirty-one modules in a system.

Axon Architecture

The Axon Architecture provides power, system synchronization and communication facilities between all the system modules. There are three hardware components which comprise the Axon Architecture: the Base Board (FIG. 3)/Adapter Module of the Compute Module; the Neuron Board (FIG. 4) in each functional module; and the Axon Cable which interconnects each module.

Figure 3:
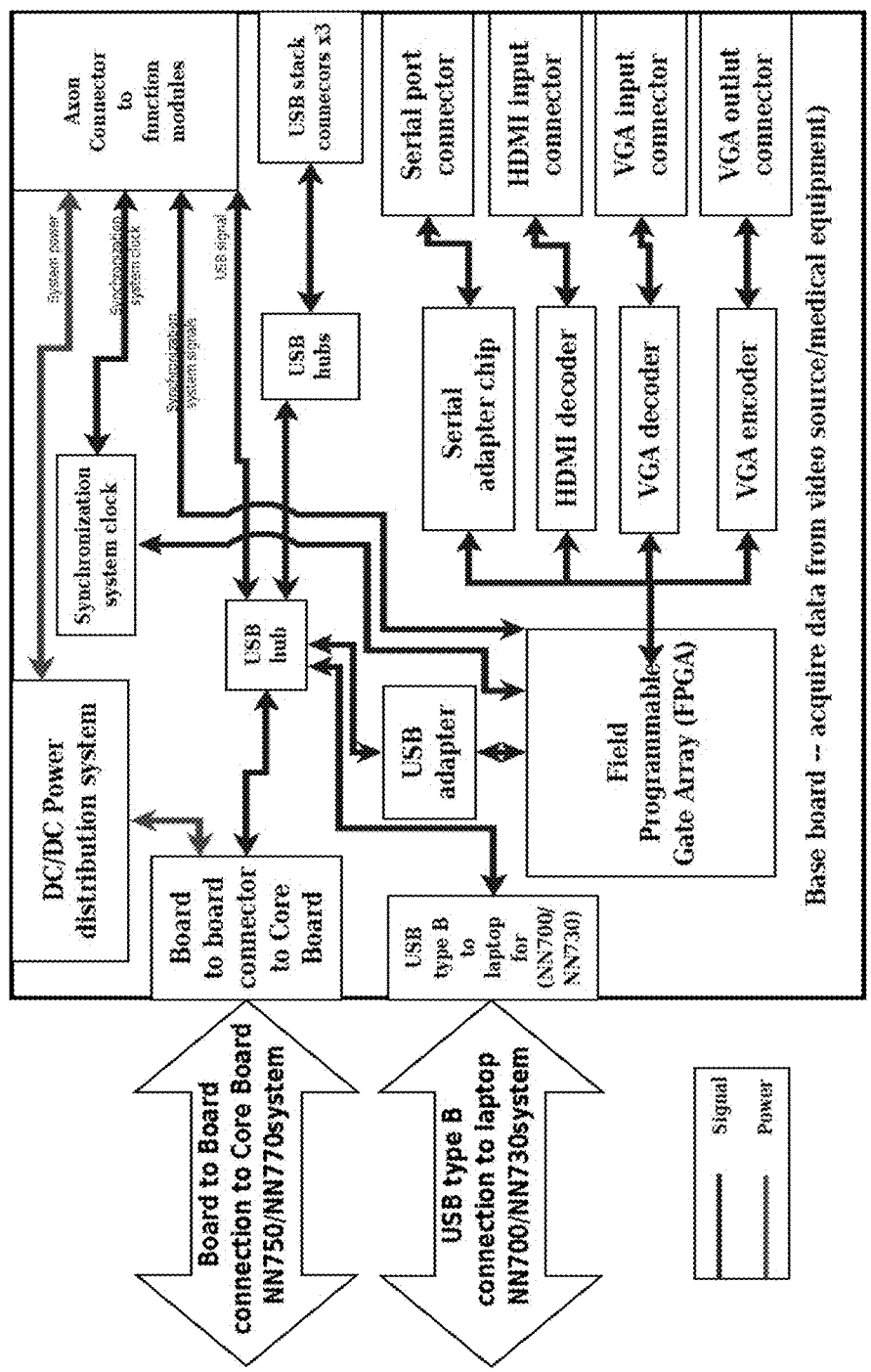
FIG. 3 is a schematic of the Base Board (BN7-U003), with red lines indicating power distribution and blue lines information distribution, in accordance with an embodiment of the invention.
Figure 4:
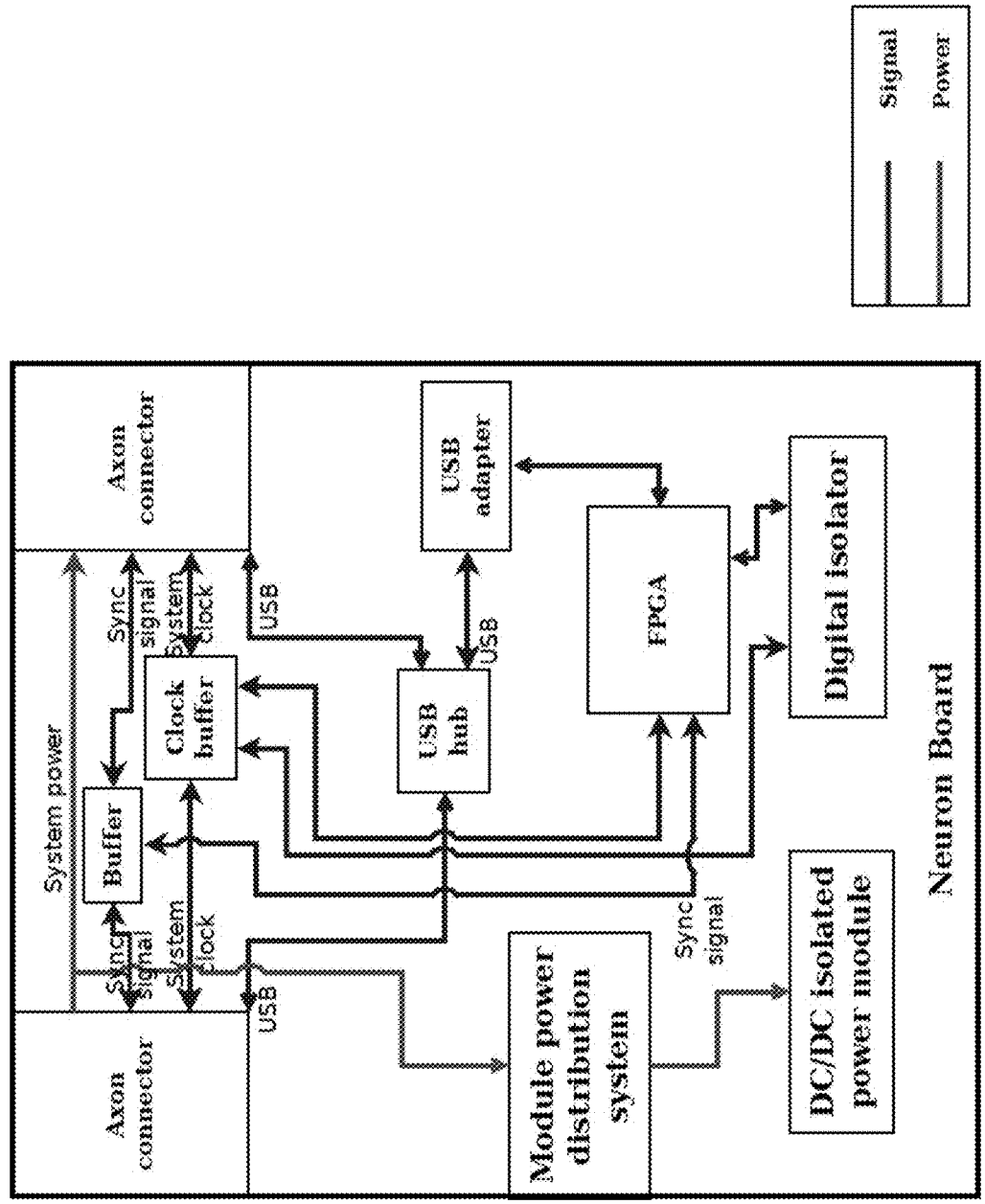
FIG. 4 is a schematic of the Neuron Board (BN7-U001), providing universal control and communications, with red lines indicating power distribution and blue lines information distribution, in accordance with an embodiment of the invention.

In order for the Compute Module to be able to control and retrieve data from the functional modules directly with minimum communication complexity, the USB protocol and USB hub architecture is used in the chain of modules as shown in FIGS. 3 and 4. Thus there is one USB hub and one USB adapter on each Neuron Board to provide a USB interface for the current module and the next connected module. With this structure, all the functional modules connected are recognized by the Compute module as USB devices. A proprietary USB communication protocol allows the Compute Module to control and configure the functional modules.

Base Board

The Base Board (FIG. 3) (BN7-U003) is designed to provide three functions: data concatenation, system synchronization of the functional modules with a 32.768 MHz clock and an interface between the Compute Module and the function modules which provides the correct data format looking towards either device. The Base Board is an FPGA based multi-media data acquisition board which can acquire data from multiple sources in the operating room, such as video, images and the anesthesia monitor. To support these functions, it contains HDMI, VGA and Serial Adapter chip sets to support data capture. It has three video connectors: an HDMI input port, a VGA input port, and a VGA output port. The data are encapsulated by the FPGA and sent to the core board through the USB connection. The data from the video and imaging sources and the anesthesia machine are encapsulated and broadcast for viewing.

Neuron Board

The Neuron Board (FIG. 4.) (BN7-U007) provides the interface to the Axon-Cable for the functional modules and supports the USB communications, manages power to the module, and contains a field programmable gate array (FPGA) which controls the function of the module it is in. The Neuron Board provides for module power distribution, module control/data transmission, system synchronization, and controls data retrieved from a specific functional module, such as the data acquisition board of a Data Acquisition module, electrical stimulation board for an Electrical Stimulation module, and visual/auditory stimulation board for visual/auditory stimulation module. A USB 3.0 controller chip is utilized on the Neuron Board to serve as a USB signal adapter between the FPGA chip and the Compute module.

Axon Cable

The Axon-Cable (FIG. 2) provides the interconnection between the modules and provides power as well as all communications between the modules. Table 3 shows the power/signal pins connected in the Axon-Cable. The Axon cable needs to be able to deliver a 5 Amp current at 24 volts. The communication includes two parts: the clock signal for synchronization of all the functional modules and the control/data transmission. The control/data transmission is implemented using the USB protocol. In NeuroNet-VII system, the Compute Module utilizes USB protocol to control/configure the functional modules and retrieve data from them. The system synchronization protocol and the control/data transmission protocol are described below.

TABLE 3

Axon-Cable Power/Signal Connector Specifications

| USB Type-C Plug #1 Upstream Connector Pins | USB Type-C Plug #2 Downstream Connector Pins | Signal |
|---|---|---|
| A1, A12, B1, B12 | A1, A12, B1, B12 | GND |
| A4, B4, A9, B9 | A4, B4, A9, B9 | POWER |
| A2, B2 | A2, B2 | USB 2.0 D+ |
| A3, B3 | A3, B3 | USB 2.0 D− |
| A5, B5 | A5, B5 | Single ended reference signal |
| A6, B6 | A6, B6 | System synchronization control +(reserved) |
| A7, B7 | A7, B7 | System synchronization control −(reserved) |
| A8, B8 | A8, B8 | Single ended system trigger signal |
| A10, B10 | A10, B10 | System clock CLK+ |
| A10, B10 | A10, B10 | System clock CLK− |
| Shell | Shell | Shield |

The design utilizes USB type C receptacle as the Axon-Cable connector in the modules. This receptacle meets the power/signal transmission requirements and allows the utilization of a standard receptacle with a unique interconnecting cable. The USB type C plug is also utilized at both ends of the Axon-Cable, which are additionally identified as upstream or downstream connectors. Signal integrity and system stability require that all the signal differential pairs are twisted and individually shielded. The cable also has an outer shield.

System Synchronization Protocol

Figure 5:
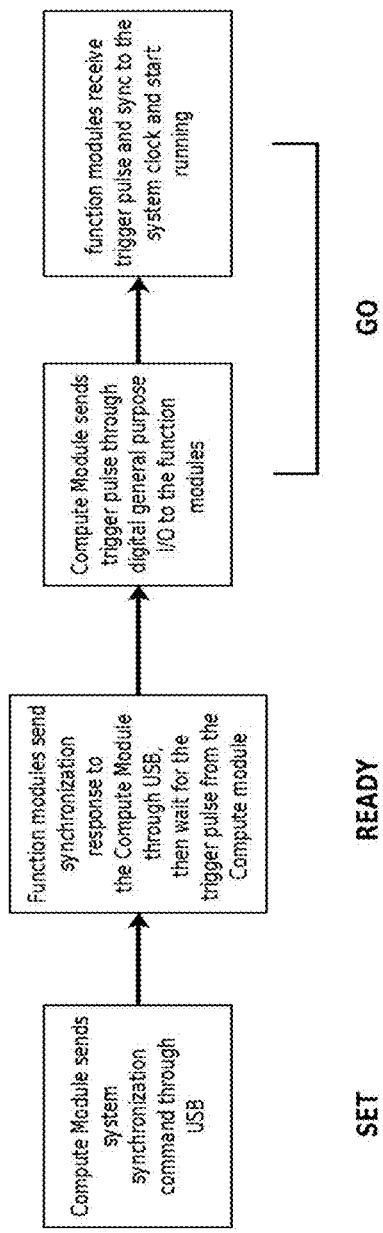
FIG. 5 is a diagram of the System Synchronization Protocol, in accordance with an embodiment of the invention.

NeuroNet-VII requires near real time operation in that the acquired data from each data channel is required to be synchronized within 62.5 μsecs for each data sample and stimulus. This ensures that all data are aligned for processing. However, the Compute Module is running a non-real time operating system while the FPGA chips with each functional module, which are responsible for stimulus presentation and data acquisition, have no operating system. To meet this system requirement a synchronization method has been developed which utilizes a system synchronization clock, on the Base Board (FIG. 3) (BN7-U003), which provides a common synchronization signal to each functional module. Therefore the Base board and the functional modules are running under the same clock. The USB control signal (USB 2.0 D+/−), the digital control signals, and the synchronization clock (System clock CLK+/−) are listed in Table 4. The details of this innovative method are shown in FIG. 5 and are as follows:

(1) System synchronization request: To start the system synchronization procedure, the user issues an Acquire Data command which requires system synchronization. The Compute Module then sends a USB system synchronization command to the functional modules.

(2) Functional modules response to synchronization request: When the functional modules receive the system synchronization signal, they send a response back to indicate that the modules are ready for system synchronization. Then the modules detect the digital logic trigger signal for synchronization.

(3) Digital logic signal for synchronization: After the response message from the function modules is received, the Compute Module sends a digital logic pulse through its general purpose input/output pins to the functional modules. The functional modules are running at higher clock rate and, thus, are able to detect the digital pulse from the Compute Module. Once the trigger pulse is detected, the functional modules reset their internal counters and all the registers to start all modules of the system with the same initial time.

Control/Data Transmission Protocols

NeuroNet-VII utilizes the USB protocol and USB hub structure to support communications between the daisy chained modules. Within this architecture, all the functional modules connected are recognized by the Compute Module as USB devices.

The standard USB hub structure allows up to 7 cascading tiers of devices. The NeuroNet-VII design has this same limitation; however, the NeuroNet-VII design allows branching of devices which may increase the total number of devices to thirty-one.

Figure 6:
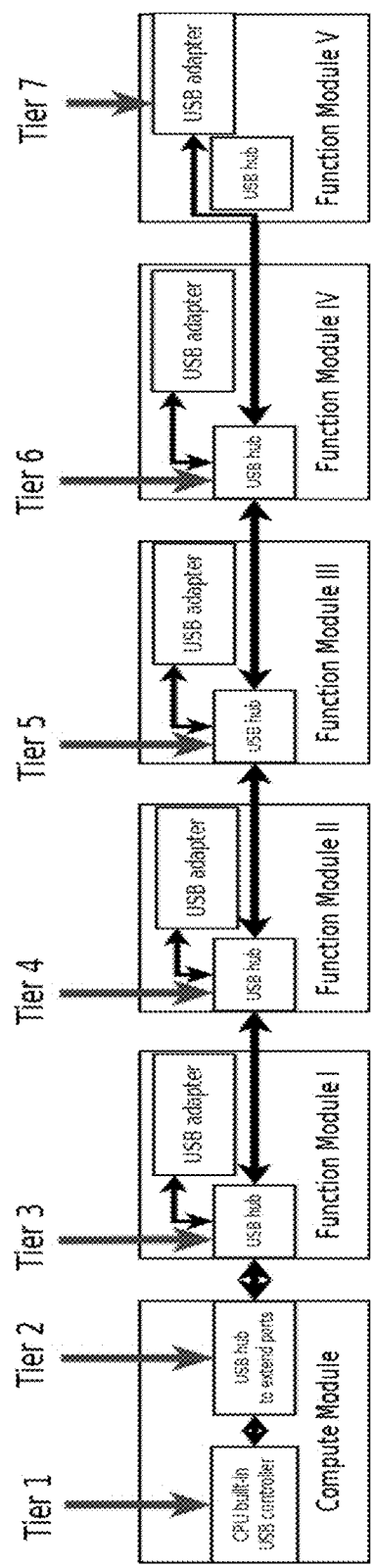
FIG. 6 shows the USB hub structure for the Axon Architecture which allows for 5 functional modules, in accordance with an embodiment of the invention.

In the NeuroNet-VII design each tier, except the last (the 7th), is defined by a USB hub, which provides ports for devices in the next higher tier to connect to (FIG. 6). The USB root hub (Tier 1) is directly attached to the USB host controller in the CPU chip of the Core module. The Compute module contains a second hub (Tier 2), which is a device to the Tier 1 hub, and which provides ports for interconnecting to the next module in the chain (Tier 3). Thus, the functional module 1 has a Tier 3 USB hub which connects to a Tier 4 USB adapter located on the same module and a Tier 4 USB hub located on functional module 2. In a fully configured system, the 5th module which is at Tier 7 in the serial chain appears as a device to the Tier 6 USB hub, to meet the USB standard. The portable configuration (laptop based) contains the USB root hub/controller combination in the laptop while the Tier 2 hub is contained in the Base/Brick board (BN7-U003) which provides the interface between the laptop and the downstream modules.

The System design requires the modules to be arbitrarily serially connected in any order, with no requirement as to which module must be last in the chain. Each module has the same Communication board which contains a hub. Thus, to ensure that whichever module is Module 5 (Tier 7) in a chain, the system senses if another module is connected downstream and provides both a guaranty that no more than five modules are serially connected and that there is a switching mechanism to ensure that Module 5 appears as a device.

Figure 7:
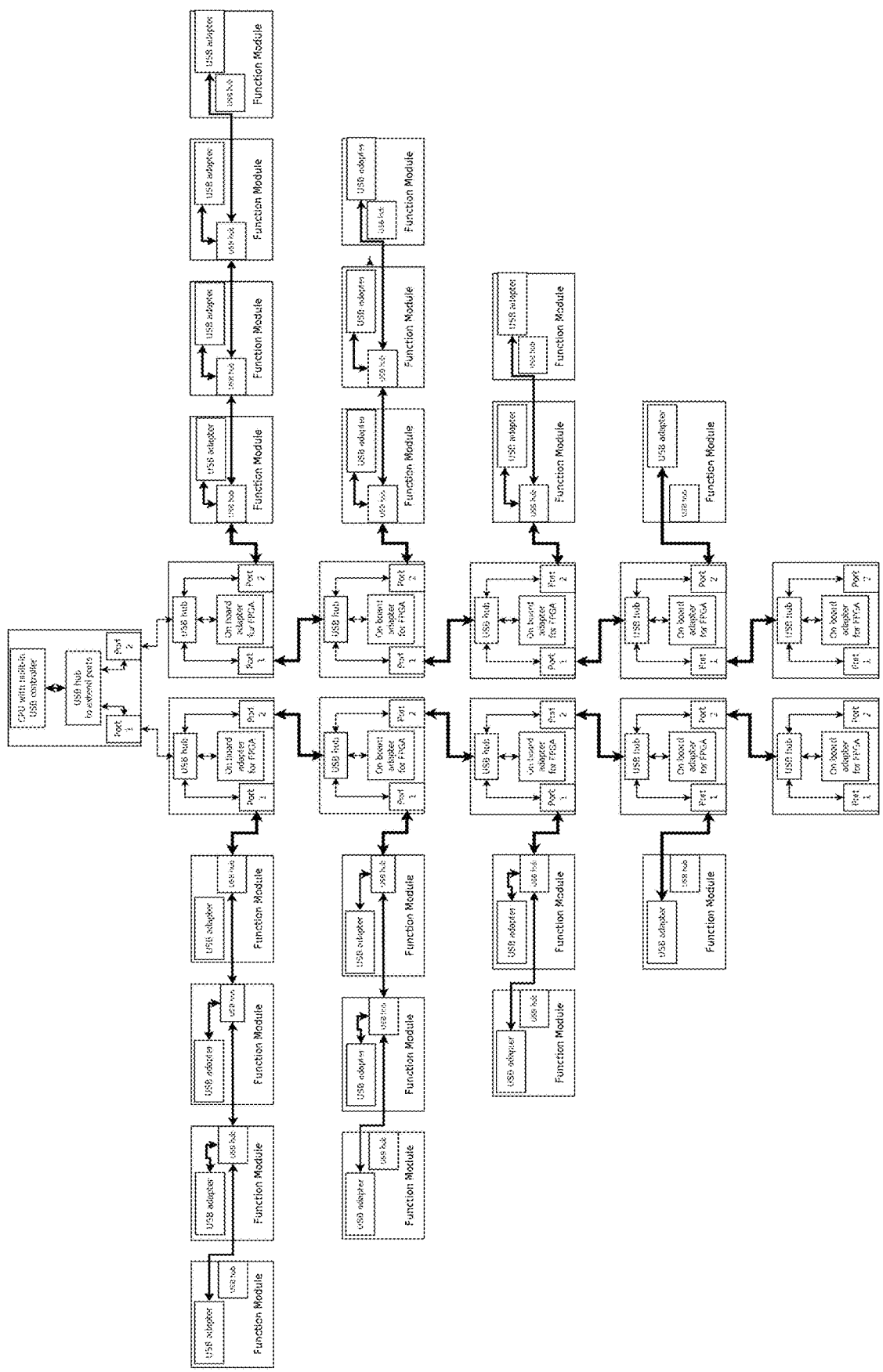
FIG. 7 shows the USB hub structure for the Axon Architecture which allows for up to 31 functional modules, in accordance with an embodiment of the invention.

Modules may be connected into a single system based on the branching architecture as shown in FIG. 7.

Switching Circuit to Implement the USB Hub Architecture

A fully configured NeuroNet-VII system has five modules: three Data Acquisition modules, one Electrical Stimulation module, and one Auditory/Visual stimulation module. As discussed above, the system design requires a switching circuit in each module which can detect if another downstream module is plugged in or if the module is the last module in the serial chain. If a module is determined to be the last module in a serial chain, the USB hub in that module switched out of the circuit making the controller on that hub the last device in the chain. If a particular module is not the last one in the chain of modules, then the switching circuit includes both the hub and the controller as devices for that Tier level. To achieve this, the design has a USB switching circuit within each module to dynamically choose between including the USB hub in the signal path or not. In either case the USB controller is maintained in the signal path since it provides a bidirectional signal path to the FPGA chip.

Figure 8:
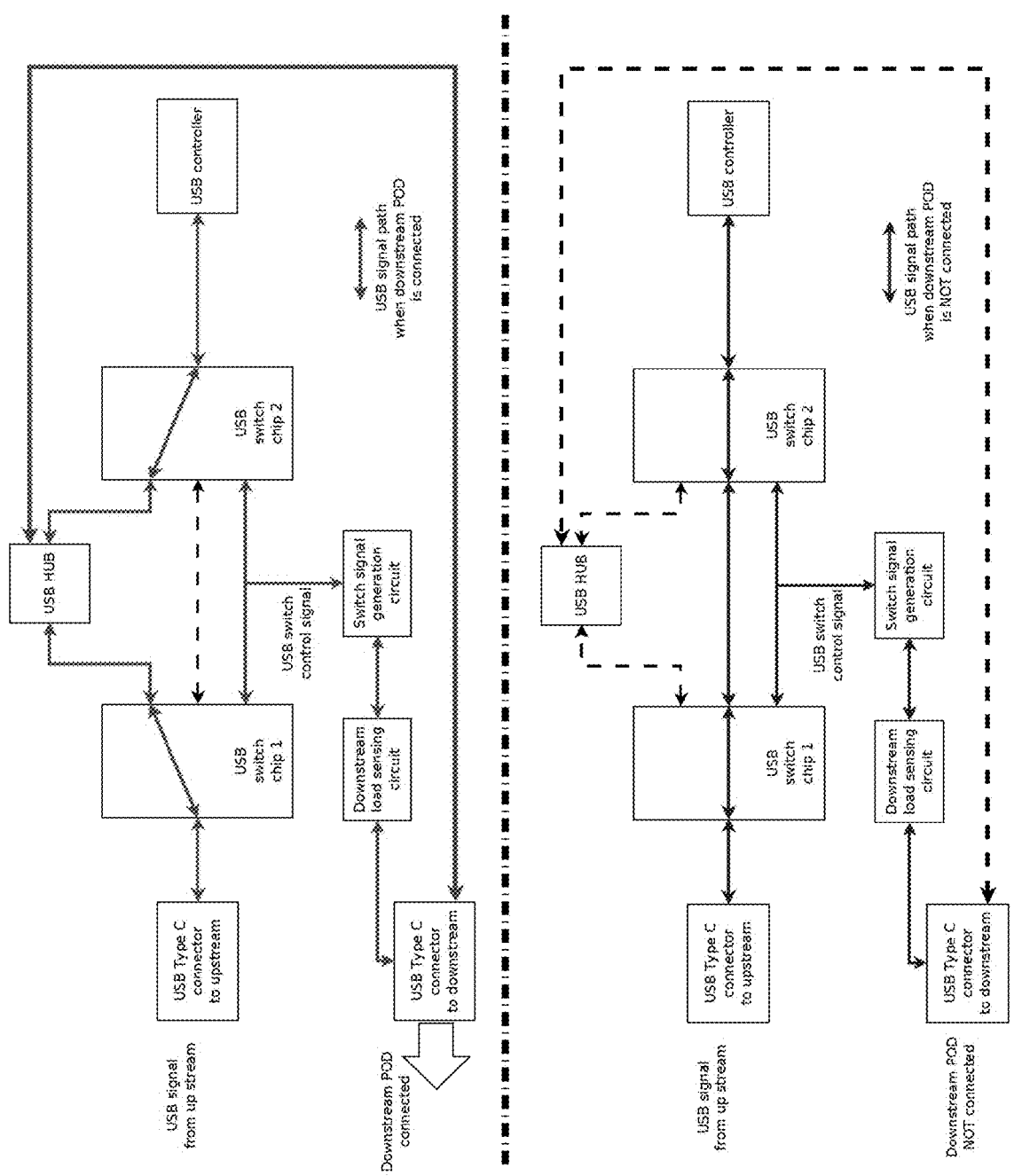
FIG. 8 shows the USB switching circuit design, where (Top Panel) is a downstream module connected and (Bottom Panel) is a downstream module not connected, in accordance with an embodiment of the invention.

The switching circuit is triggered by whether the downstream port is loaded or not. Loading is detected by sensing a current on the Ground wire (Pair 5) of the USB connector. If the downstream port is loaded, the USB hub is selected unless the functional module is the 5th in the chain. The USB switching circuit is shown in FIG. 8. In this design, the power load from the Axon Connector is detected. If there is one or more functional modules connected to the system after a particular module, the power and ground pin of the Axon cable would have a load current since the downstream modules get power from the Axon-Cable power and ground wires. The load current is detected and utilized to generate a detection signal. This detection signal is then used to drive the selection signal of the multiplexer circuit on board. The multiplexer circuit shall then switch its connection channel between the USB hub and the USB adapter chip. If a 6th serial module is placed in the chain, the application layer of the software issues a warning to the user that the module will not function and issues a control signal to the switching circuit functionally disconnecting the 6th serial module.

Compute Module

Figure 9:
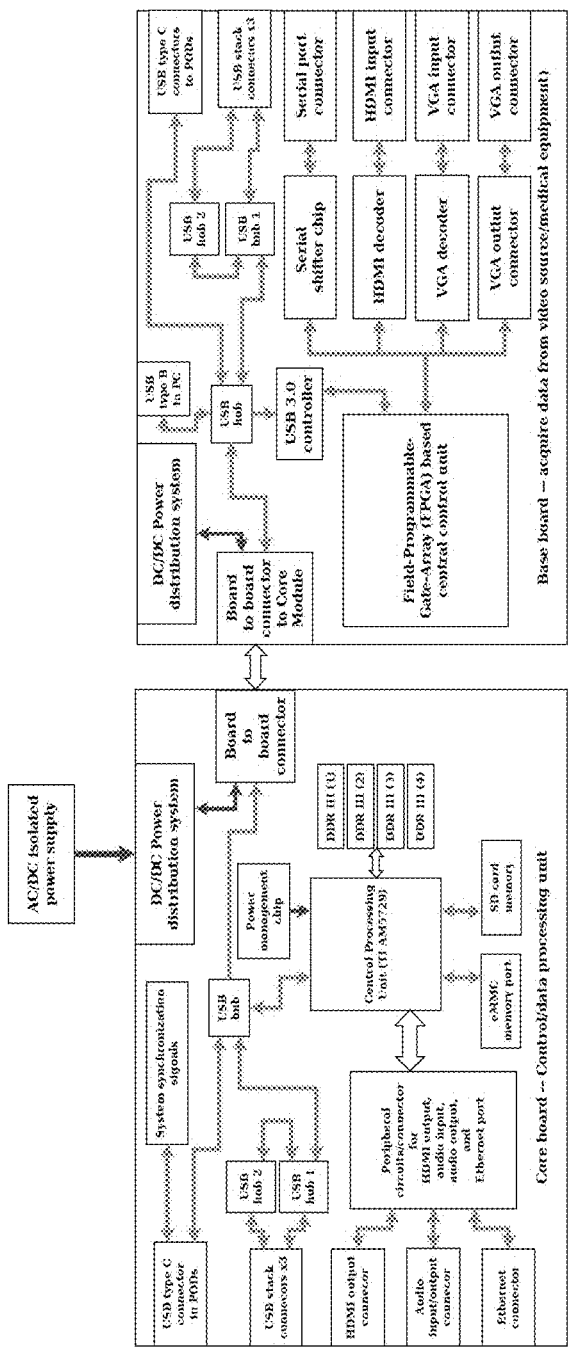
FIG. 9 is a schematic showing the Compute Module A, where (Left Panel) shows the Core Board and (Right Panel) shows the Base Board, with red line showing power distribution and green lines showing information distribution, in accordance with an embodiment of the invention.

Referring now to FIG. 9, the Core Module is structured as the data processing and central computation unit of the Neuronet-VII system, which uses a Linux based operating system. A laptop serves the same functions for the portable version of the system. The Compute Module consists of two boards: Core Board (BN7-C001) and Base Board (BN7-U003). The Core Board (FIG. 9 Left Panel) is the central control and data processing board. It provides the interface to the modules via a USB type C connector and customized system daisy chained cable. The Core Board receives data from the modules and configures/controls the modules under a USB protocol. The Base Board (FIG. 9. Right Panel) provides a video interface to acquire video data from an operating microscope and endoscope. It also provides a serial port interface to capture data from an anesthesia machine. The video frame data and anesthesia data are transmitted to the Core Board through a USB connector between the Core Board and the Base Board.

Core Board

The Core Board (BN7-C001)(FIG. 9 Right Panel) receives data from the modules and Base Board (BN7-U003). Once the data are received, the Core Board processes, displays, and stores the data. A Linux based operating system runs on the Core Board and manages all computational processes. Neuro, the System's software application layer, is executed on top of the operating system and provides all user interfaces and originates all control signals to the system for operation. The Core Board is an artificial intelligent embedded core enabled computer board. It has an ARM-based CPU, which has two ARM Cortex-A15 cores, one embedded digital signal processing core and an embedded micro-controller core. The Core Board reduces the risk of hardware compatible issues which are a problem with commercial computers. In addition, the Core Board also provides an audio interface for a proprietary designed speaker module with audio power amplifier, an ethernet port, a HDMI video port, and enough USB ports for multiple system accessories. A WiFi/BLUETOOTH® module also is embedded on the Core Board, which makes the Core Board capable of communicating with BLUETOOTH® enabled devices and to connect to an available WiFi network. The wireless module also allows the system to be controlled by a BLUETOOTH® enabled tablet. This configuration allows the system to be controlled remotely and for the data to be easily shown to the surgeon.

Base Board

The Base Board (BN7-U003) (FIG. 9 Right Panel and FIG. 3) is previously described above.

Integration of Operating Room Video Imaging Data into the Signal Chain

The Base Board contains HDMI and VGA chipsets to support different input formats from possible video sources and imaging equipment. As shown in FIG. 3, there are three video connectors: an HDMI input port, a VGA input port, and a VGA output port. The two input ports are used to capture video from an operating microscope or endoscope. The video frames are collected and integrated into neurological signals into the system, which is used for signal analyzing and patient diagnosis. The VGA output is utilized to export collected signals as video stream which can be integrated with the neurophysiological data and injected into the operating microscope for real time visual feedback.

Integration of Anesthesia Data into Signal Chain

Anesthesia data is critical for IONM, as anesthesia levels affect the data. The Base Board (FIG. 3) contains a serial port which allows the system to obtain data from an anesthesia machine. The data is collected and integrated together with the other signals for local and remote display as well as for archiving as part of the case record.

Integration with Laptop

The portable Neuronet-VII system utilizes a laptop as the computing unit for data processing, displaying and storage. Since the system is designed as a daisy chained system, not only are there standard USB signals within the interconnecting cable, but also power (Pair 4), ground (Pairs 5 and 6), system clock (Pair 2), and system synchronization signals (Pair 7) in the cable [Table 3]. Therefore, the daisy chained modules, though based on the USB networking standard, cannot be connected directly to the USB type C port of a commercial computer. The Base Board provides an interface between the laptop and the daisy chained modules; i.e., this interface provides a compatible daisy chain port to the downstream modules and compatible classic USB interface to the upstream laptop. As shown in FIG. 3, the Base Board provides a USB type C port to the downstream s modules and a USB type B port to the upstream laptop. The Base Board is recognized by the laptop as a USB device. Thus, the USB hub structure on the Base Board provides the USB connection from the modules to the laptop. The Neuro software application running on the laptop executes the same as on the Core Module.

Data Acquisition Module

Figure 10:
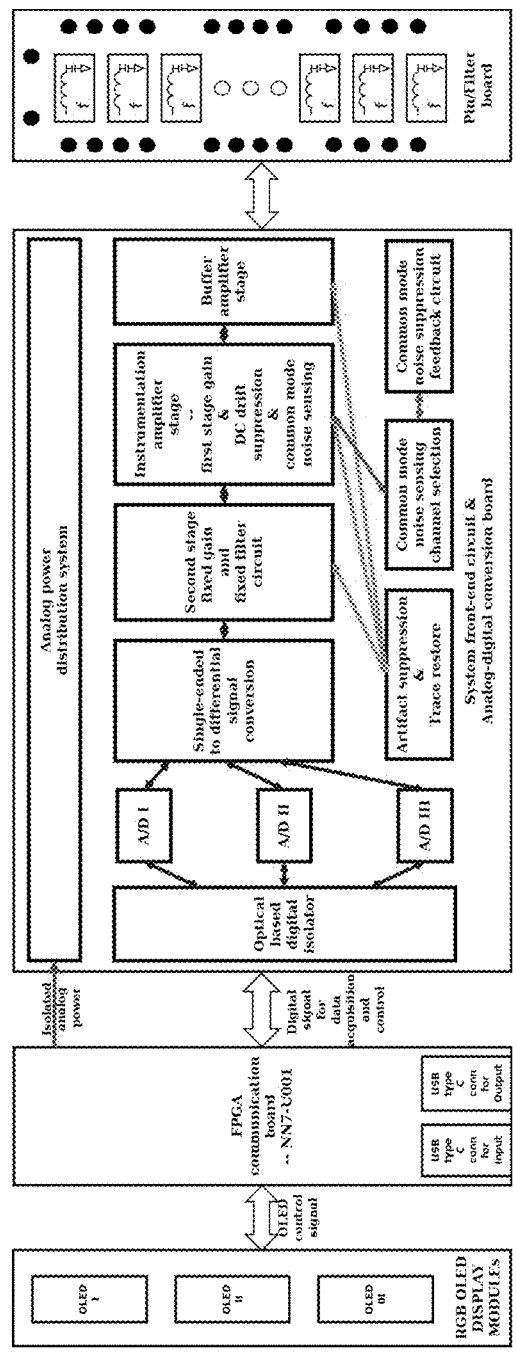
FIG. 10 is a schematic showing the data acquisition module structure, in accordance with an embodiment of the invention.

The Data Acquisition Module is designed to acquire all types of neurophysiological data which range from 0.1 μvolt to 1000 μvolts in amplitude. As shown in FIG. 10, the structure of the Data Acquisition module comprises: (1) Pin/Filter board (BN7-A002); (2) 24 Channels of amplification with DC drift suppression, feedback noise suppression, and A/D conversion (Bn7-A001); (3) OLED Display board (BN7-U002); and (4) a Neuron board (BN7-U001).

The present invention provides significant innovations which are included in the Data Acquisition module: (1) an electrosurgery suppression filter that eliminates high frequency and high voltage noise from an electrical surgical knife (i.e. Bovie); (2) common noise suppression filter based on feedback to patient; (3) DC drift correction; (4) Signal Blanking with stimulus presentation; (5) OLED channel identification; and (6) Digital differencing.

Electrosurgery Suppression Filter

Electrosurgery is widely used in surgical procedures. However, electrosurgery is problematic because the high frequency (300 kHz-500 kHz)/high voltage (300V~500V) current utilized in these devices is noise from the monitoring perspective which fully saturates prior art systems.

The electrical properties of active components, such as operational amplifier, instrumentation amplifier, and analog-to-digital converters cause active components to be saturated once the input signal is out of range of power input range. Therefore, whenever the surgeon uses an electrosurgery device, the high frequency and high voltage signal saturates the signal pathways, making it impossible to continue recording essential biological/neurological signals from the patient. The signal obtained during the time that an electrosurgery device is being used is noisy, saturated and unsuitable for interpretation.

Even though the signal will return to normal once the electrosurgery device stops operating, it is still important to know what is impacting the nervous system while the device is being used. The present invention provides a front-end filter that eliminates the noise injected by the electrosurgery device, and thus allows the continual recording of essential neurological signals. The front-end filter of the invention is unique and is the first and only such filter incorporated into a system of this type.

Filter Design

The electrosurgery device produces a signal which has a frequency range from 300 kHz to 500 kHz with a 300V 500V signal amplitude. The frequency range of the biological/neurological signals that the invention focuses on are from DC to 3 kHz. An additional constraint is provided by the minimum amplitude of the signals that need to be acquired. The brainstem auditory evoked potentials (BAP) signal is about 0.2 uV peak-to-peak which defines the amplitude of this minimum signal.

Figure 11:
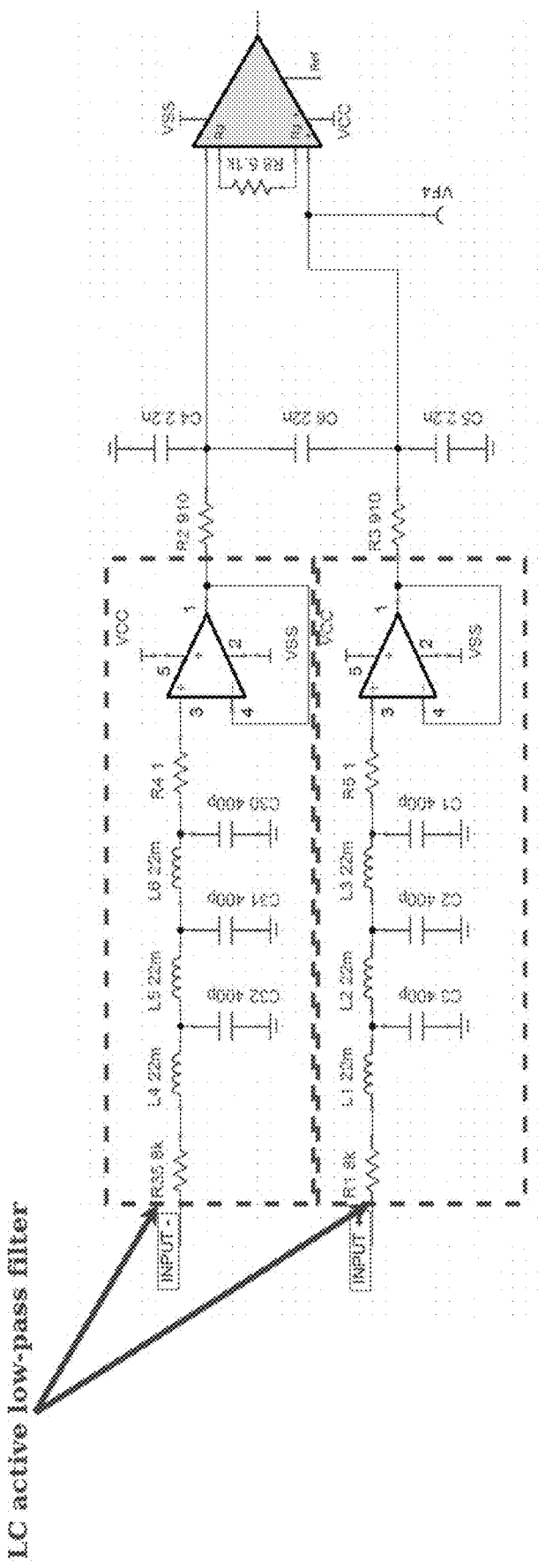
FIG. 11 is a schematic of the third order LC active electrosurgical suppression filter, in accordance with an embodiment of the invention.
Figure 12:
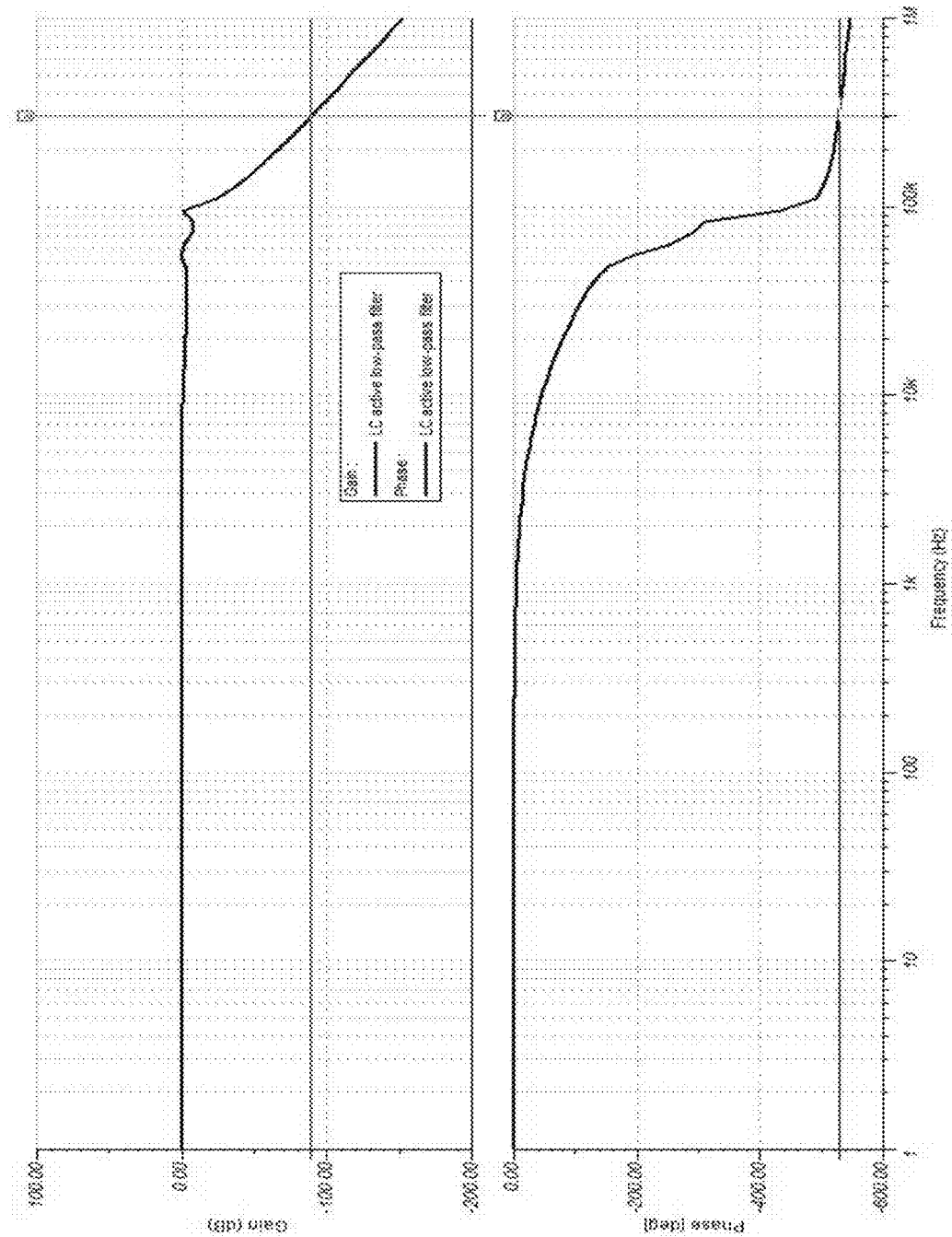
FIG. 12 are two frequency response curves of the electrosurgery suppression third order LC filter, where (A) demonstrates amplitude response which is flat to 50 kHz, and (B) demonstrates phase response which has 0° phase shift to 3 kHz, in accordance with an embodiment of the invention.
Figure 13:
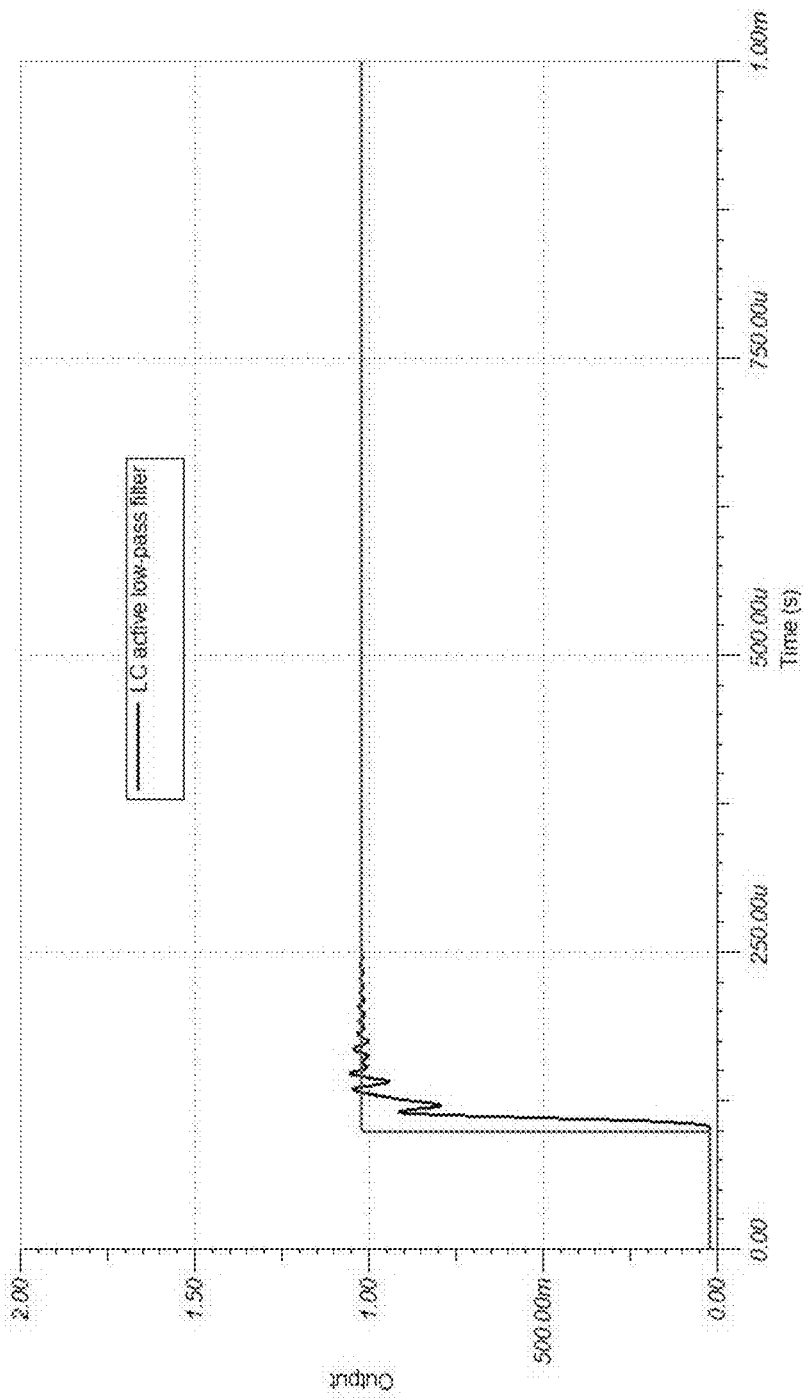
FIG. 13 shows the transient response for the 3-pole active LC filter, in accordance with an embodiment of the invention.
Figure 14:
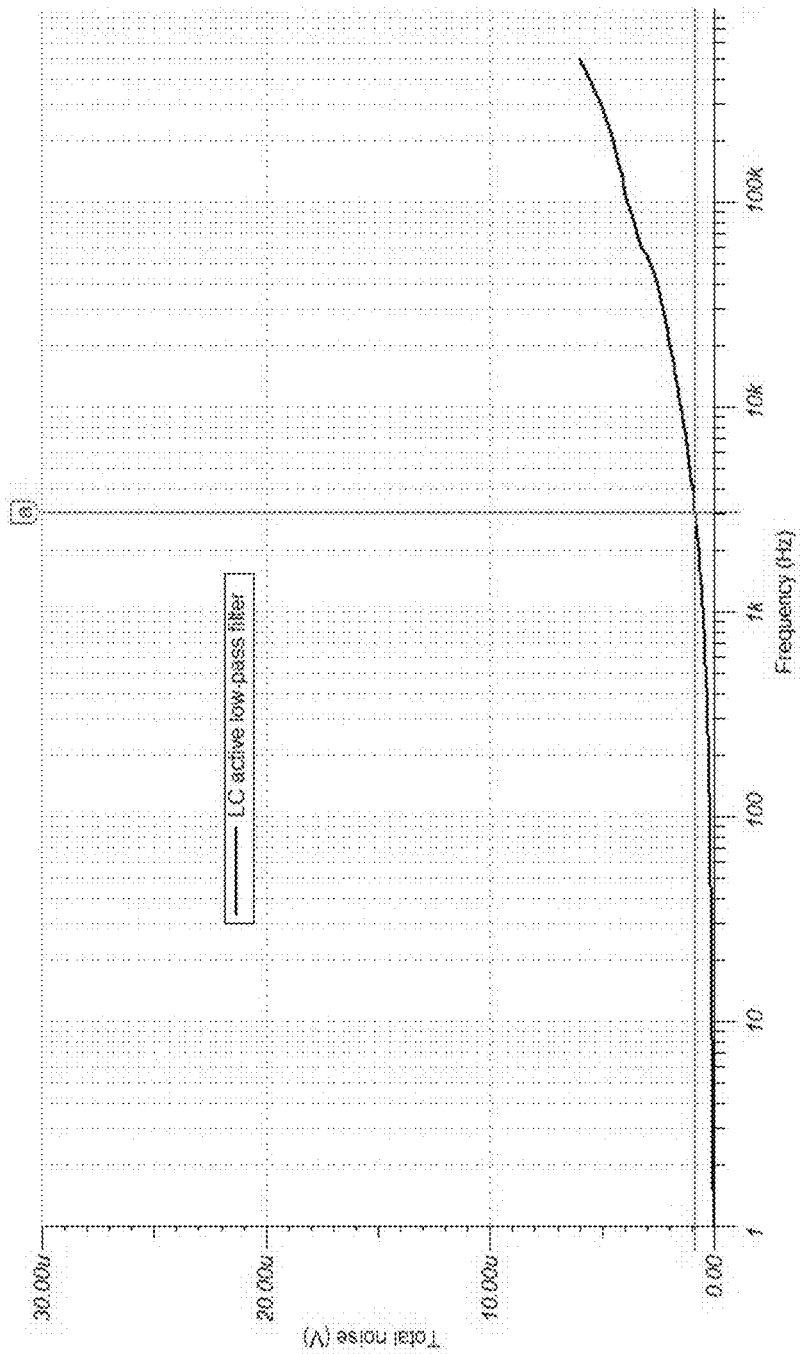
FIG. 14 shows noise analysis of the electrosurgery suppression filter, in which the blue line shows the noise produced by the filter as a function of frequency, in accordance with an embodiment of the invention.

In order to suppress the electrosurgery signal and preserve the signal the user is interested in acquiring, the present invention provides a low pass filter with more than about −60 dB suppression at 300 kHz and 0 dB at less than about 3 kHz. A resistor based resistor-capacitor (RC) low pass filter is not suitable due to the high thermal noise this design produces compared to the signal requirements. Based on the above considerations, the present invention provides a unique inductor-capacitor (LC)-based third order active electrosurgical suppression filter, shown in FIG. 11, which provides the low thermal noise frequency bandpass properties required for continued signal acquisition without saturation while an electrosurgery device is being used. In addition, the frequency response, transient response and noise analysis of this filter are shown in FIGS. 12-14, in which FIG. 12 shows the frequency response curve (amplitude and phase shift) of the filter; FIG. 13 shows the transient response for the filter, in which the rise time is less than 25 psec; and FIG. 14 shows the noise analysis of the filter.

Feedback Common Mode Noise Suppression

Many devices in the operating room generate common mode noise, such as 60 Hz power line noise and radio frequency noise, which should be canceled with differential input amplifiers. However, in the prior art the front-end circuits contain resistors, capacitors, inductors, and other passive/active electronic components have levels of inaccuracy which provide imbalance in the signal pathways. Thus, common mode noise still remains in the system after the basic differential operation. The present invention provides a unique method utilizing feedback to the patient of the noise component of the signals being measured. This feedback signal balances out the common mode noise due to the input channels not being perfectly balanced and matched.

The following factors were considered in the development of this approach. Circuits with instrumentation amplifiers have high common mode rejection ratios (CMRR). In the present invention, a channel is obtained by differencing a signal electrode with the reference electrode. Therefore, the output of the instrumentation amplifier is considered to be a signal channel. To reduce the common mode noise for each channel, it is necessary to obtain common mode noise from both the positive and negative terminal of the instrumentation amplifier. From the basic three amplifier-based instrumentation amplifier (yellow amplifier) design, it is necessary to use the signal from the middle of the gain resistor (for example R1 and R2 in FIG. 15) to obtain the common mode noise signal. At this point, the common mode noise is collected without compromising the CMRR of the original amplifier.

In the invention, each Data Acquisition Module supports acquiring data from twenty-four electrodes. Therefore, it is necessary to be able to collect common mode noise from all of the 24 electrodes which are in use, and to combine them to feedback onto the patient for noise cancellation.

Figure 15:
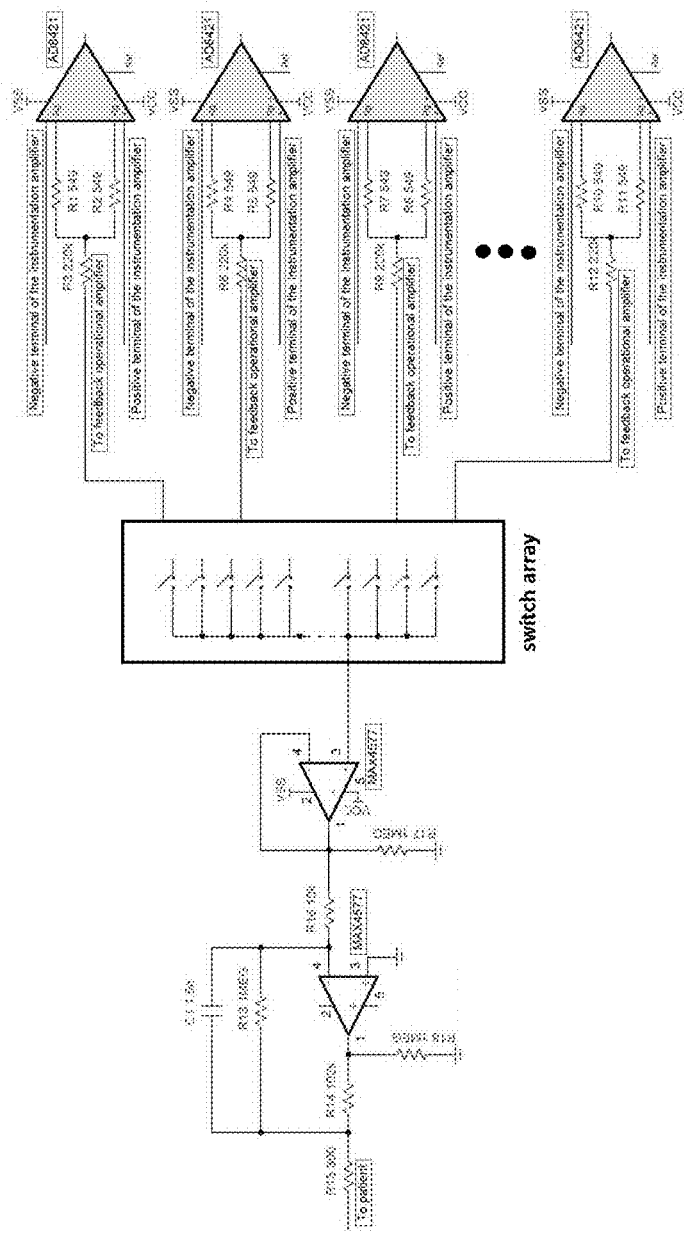
FIG. 15 is a schematic of the circuit design of the common mode noise suppression circuit, in accordance with an embodiment of the invention.

In many cases, however, not all 24 channels are in use. If these unused channels are kept in the circuit, some common mode noise not directly from the patient would be feedback and thus would itself introduce unnecessary noise onto the patient and thus into the system. Therefore, signals are selected from those channels that are used in a particular case. To accomplish this, a switching array chip is used to dynamically select channels into the common mode noise sensing loop based on which channels are activated in the Neuro software application. FIG. 15 shows the design of the common mode noise suppression circuit. In this design the sensing point uses R3 (and R6 through R12) to provide feedback to an operational amplifier which allows the noise from all 24 electrodes to be switched in and combined appropriately.

DC Drift Correction

The DC value or the baseline about which a signal drifts changes over time. This effect is called DC drift. The rate of this drift is influenced by several factors, the most significant of which is electrode polarization. This occurs at each electrode, in different quantities and at different rates, and this discrepancy in charge accumulation creates a voltage that is measured by the system (a.k.a. a battery effect). Thus, the System measures this additional voltage in series with the physiological signal.

As the polarization continues, this voltage continues to build up and the baseline value of the physiological signal changes with it. The baseline would eventually drift beyond the range of the amplifier and only a flat line would be seen in data from the amplifiers. The rate of change in the baseline voltage is on the order of that of slow cortical potentials, and thus this "battery effect" voltage can obscure very low frequency signals of interest.

There are several methods available to remove this DC drift. One common way is to introduce a blocking capacitor at the input of an operational amplifier in the acquisition system. This, however, has the undesired effect of removing low signal components as well as the drift potential.

Figure 16:
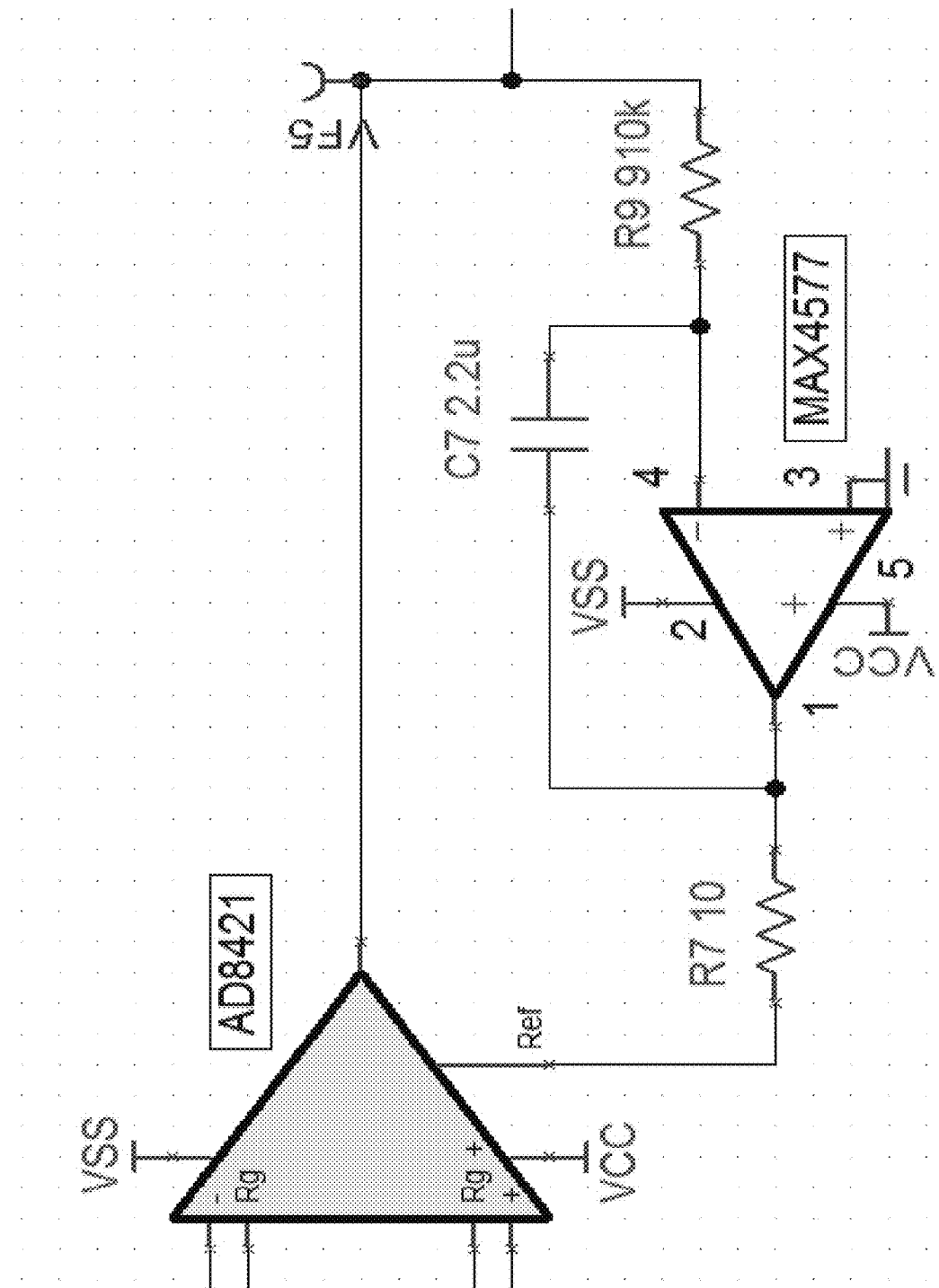
FIG. 16 is a schematic of the DC drift suppression circuit, in accordance with an embodiment of the invention.

The present invention provides an alternative design circuit, shown in FIG. 16, which accomplishes several other considerations besides eliminating DC drift. These are: (1) to retain the very low frequency components; (2) to minimize the input thermal noise, which is white noise to the system and almost impossible to filter out; (3) to ensure that the common mode noise canceling circuit is not affected by the feedback loop introduced for the drift canceling circuit. The design circuit utilizes the reference pin of the instrumentation amplifier, which is used to bias the baseline of the amplifier output to cancel the DC drift from the input. One integrator circuit is introduced to accomplish the DC drifting integration and feedback.

OLED Indicators for Electrode Identification

In the present invention, three full color OLED screens are utilized in each Data Acquisition Module to display the module number and electrode identification. The same OLED screens are utilized in the Electrical Stimulator Module and the Audio/Visual Module to identify the module and the electrodes.

Signal Differencing After Digitization

In all the prior art systems, the difference between the electrode signals is performed on the analog signals prior to digitization. This provides a remarkable limitation on the flexibility of how data channels are constructed. In this System, the electrode signals are digitized and then differenced. This provides complete flexibility as to how data channels are defined. The ith Channel is defined to be the difference between two digitized de-referenced electrode signals:

$$Chn\ i^* = ChnNSMR^* = DsigNS^* - DsigMR^* 1$$

where digitized de-referenced electrode signal, DsigNS* or DsigMR*, is the digitization of the de-referenced electrode signal, drsigNS or drsigMR. The digitization is implemented by an analog-to-digital convertor. The de-referenced electrode signal is the difference between the electrode signal and reference signal for each electrode signal:

$$drsigNS^* = esigNS^* - refsig^*$$

where esigNS is the buffered signal from the Sth active electrode in the Nth electrode module, and refsig is the buffered signal for the patient iso-ground.

Figure 17:
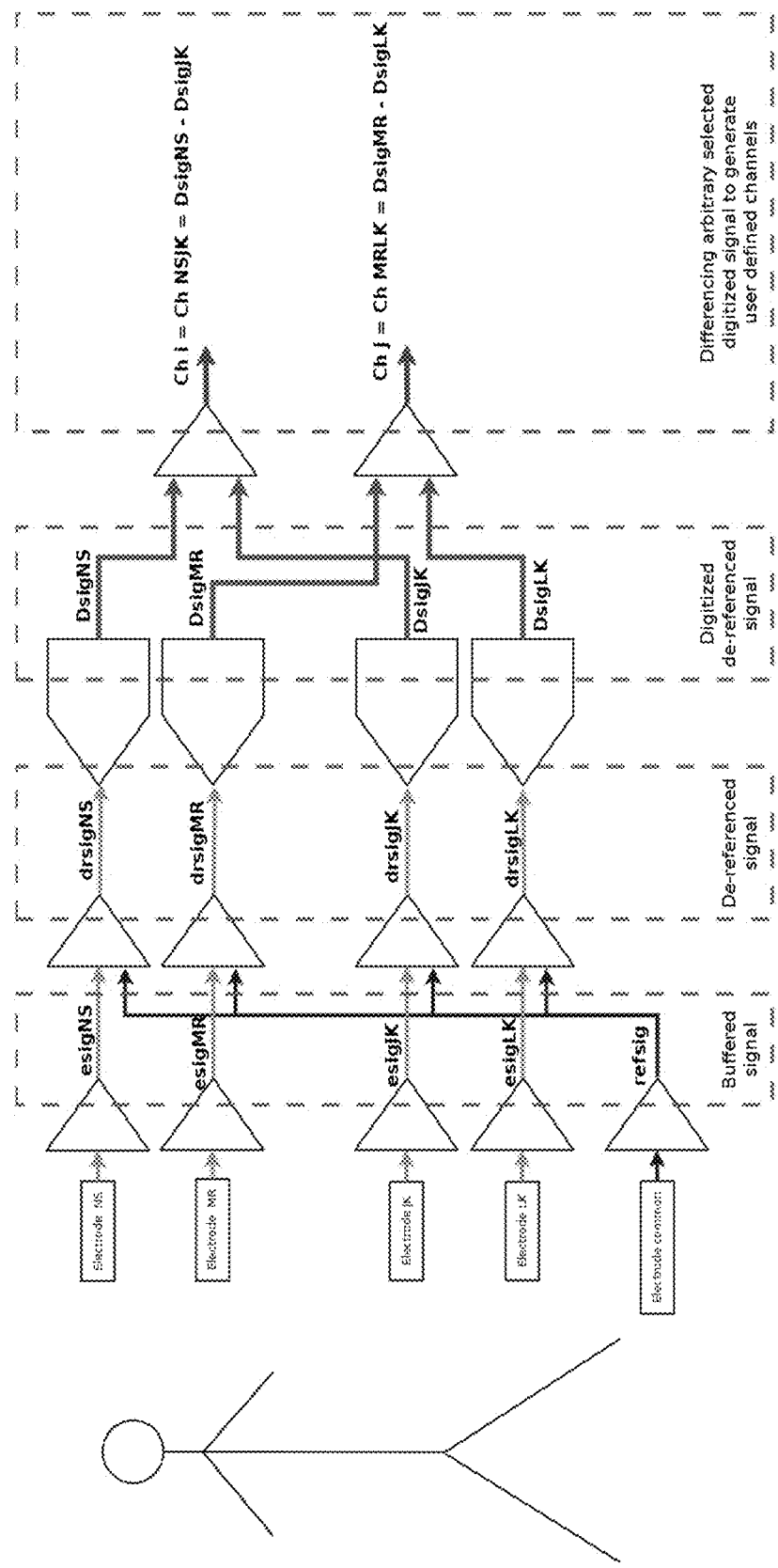
FIG. 17 is a schematic showing the differencing operation on the electrode signals to produce the desired data channel, in accordance with an embodiment of the invention.

With this method, which crosses the boundary between hardware and software, shown in FIG. 17, one can generate more channels by differencing different pairs from arbitrary electrodes of any of the Data Acquisition modules, which gives more possible ways to present data.

Stimulus Artifact Blanking Trace Restore Function

There are situations in which the input signals need to be blanked (i.e. held to ground) to prevent the amplifiers from saturating, for example when electrical stimulation is applied, most importantly with transcranial electrical stimulation to obtain motor potentials. In these situations, a stimulus artifact can be observed through the active signal paths. To eliminate the effect of these artifacts, the System provides a logic triggered signal path to pull the input terminals of different amplifier stages to analog ground in real time. This both protects the input terminals and prevents the stimulus currents from leaking into the recorded signal data stream.

Figure 18:
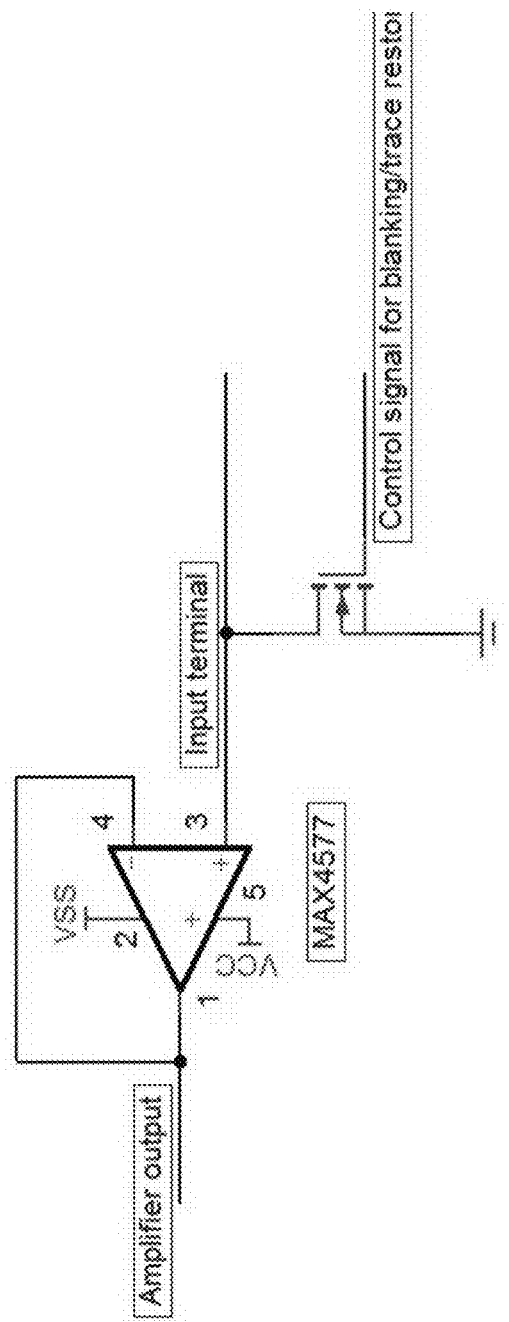
FIG. 18 is a schematic showing the MOSFET (metal oxide semiconductor field-effect transistor) based artifact blanking and trace restore, in accordance with an embodiment of the invention.
Figure 19:
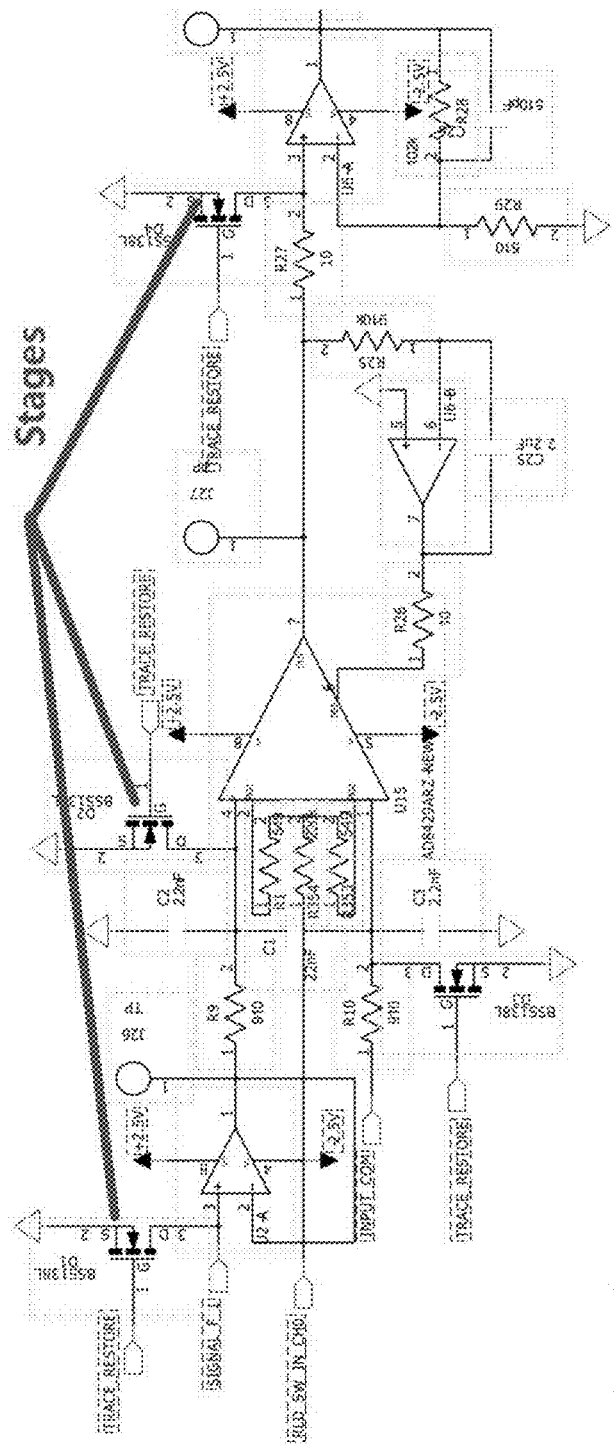
FIG. 19 is a schematic showing the multistage blanking circuit for artifact blanking and trace restoring, in accordance with an embodiment of the invention.

A second function which is accomplished by the same circuit is Trace Restore. The DC Drift Correction circuit filters out very low frequency signal, and thus the circuit has a long time constant, which requires a longer time for the signal to settle which interferes with the early signal features. Therefore, the Trace Restore circuit provides a way to settle the signal as fast as possible. The method that is used is the same as stimulus artifact blanking described above. The circuit design is shown in FIG. 18. In this circuit, an N-channel MOSFET is utilized as a controllable switch to provide a path for the signal to the analog ground. A high (logic 1) control closes the MOSFET switch, and the input terminal of the amplifier is pulled to analog ground. In normal operation (logic 0), the input terminal is the input path for the signal. Because the signal path is on all the time, this function is applied to multiple stages of the input analog circuit. FIG. 19 shows the multiple stage implementation of the inventive design for artifact blanking and trace restoring.

Stimulus Patterns

Figure 20:
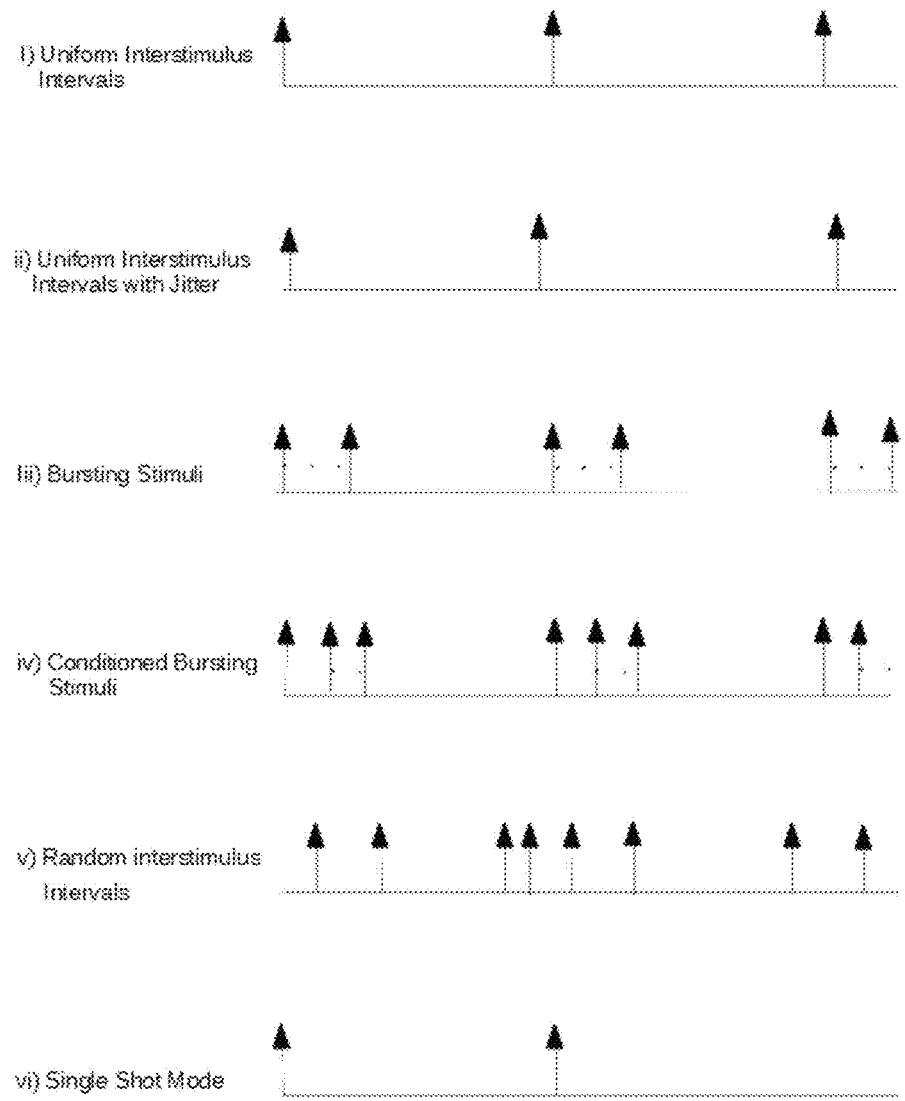
FIG. 20 shows patterns of stimuli provided by the various types of stimulators, in accordance with an embodiment of the invention.

As shown in FIG. 20, stimulators can produce a variety of train patterns for stimuli. These patterns have different situations in which they may be useful. Prior art systems produce most of these patterns except for Random interstimulus intervals.

Electrical Stimulator Module

Figure 21:
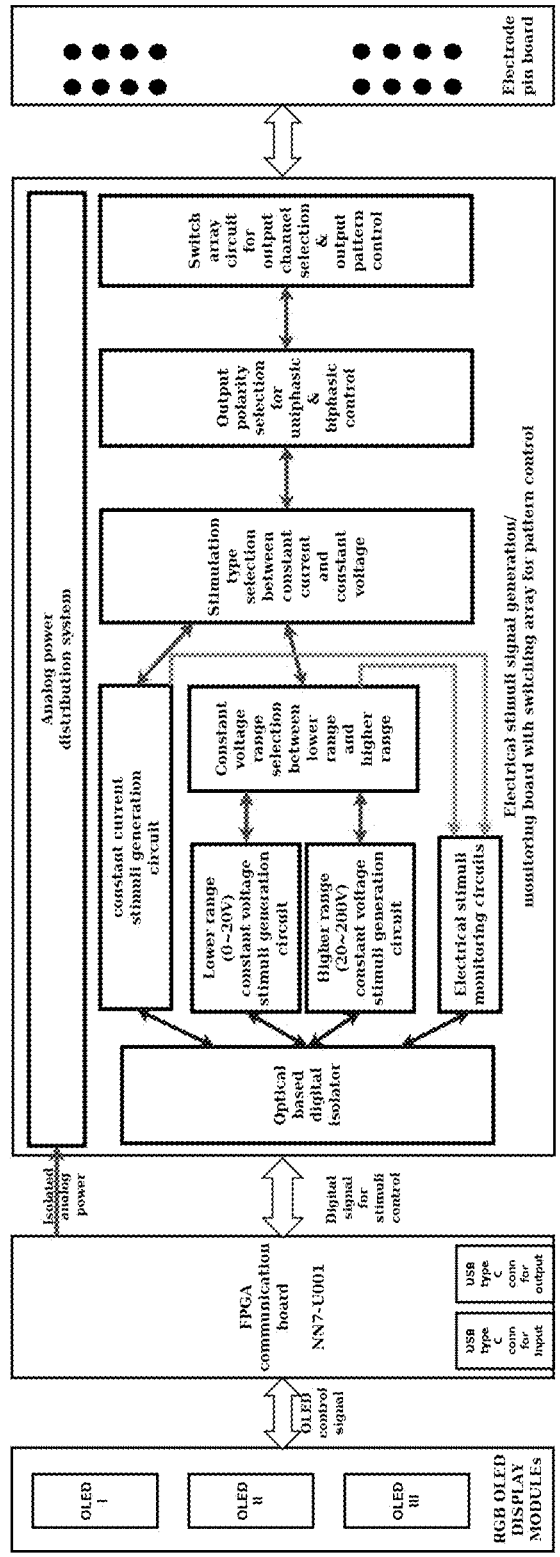
FIG. 21 shows the structure of the electrical stimulator module, in accordance with an embodiment of the invention.

As shown in FIG. 21, the Electrical Stimulator module contains four boards: a pin board (NN7-E002), a function board (NN7-E001), an FPGA communication board (NN7-U001), and an OLED board (NN7-U002). There also is an extension module (NN7-E003) which may be plugged into the stimulator module.

Constant Current Constant Voltage

Products on the market support only either constant current or constant voltage mode for electrical stimulation. The Neuronet-VII system of the present invention provides both constant current and constant voltage modes, which may be used interchangeably for stimulation. The stimulation ranges are as follows:

Constant Current

The stimulator provides three ranges of selectable stimulating currents. i) 0.1 to 20 mamps (for brain, brainstem and cranial nerve stimulation); ii) 1.0 to 100 mamps (for peripheral nerve stimulation); and iii) 1.0 to 200 mamps (for transcranial stimulation).

The constant current outputs for all three ranges have a linearity of 1%. This also is defined as the relative accuracy of the stimulators.

The constant current stimulation provides for controllable intensity levels as defined here: (i) for 0.1 to 10 mamps, 100 steps with a precision of 0.1 mamps; (ii) for 1.0 to 100 mamps, 100 steps with a precision of 1 mamps; and (iii) for 1.0 to 200 mamps, 100 steps with a precision of 2 mamps. The stimulator provides three ranges of selectable stimulating voltages: (i) 0.1 to 20 volts (for brain, brainstem and cranial nerve stimulation); (ii) 1.0 to 100 volts (for peripheral nerve stimulation); and (iii) 100 to 200 volts (for transcranial stimulation).

The constant voltage outputs for all three ranges have a linearity of 1%. This also is defined as the relative accuracy of the stimulators.

All three constant voltage stimulus levels provide for controllable intensity levels as defined here: (i) for 0.1 to 20 volts, the required step precision is 0.1 volt; (ii) for 1 to 100 volts, the required step precision is 1 volt; and (iii) for 100 to 200 volts, the required step precision is 1 volt.

Uniphasic/Biphasic Stimulation

Figure 22:
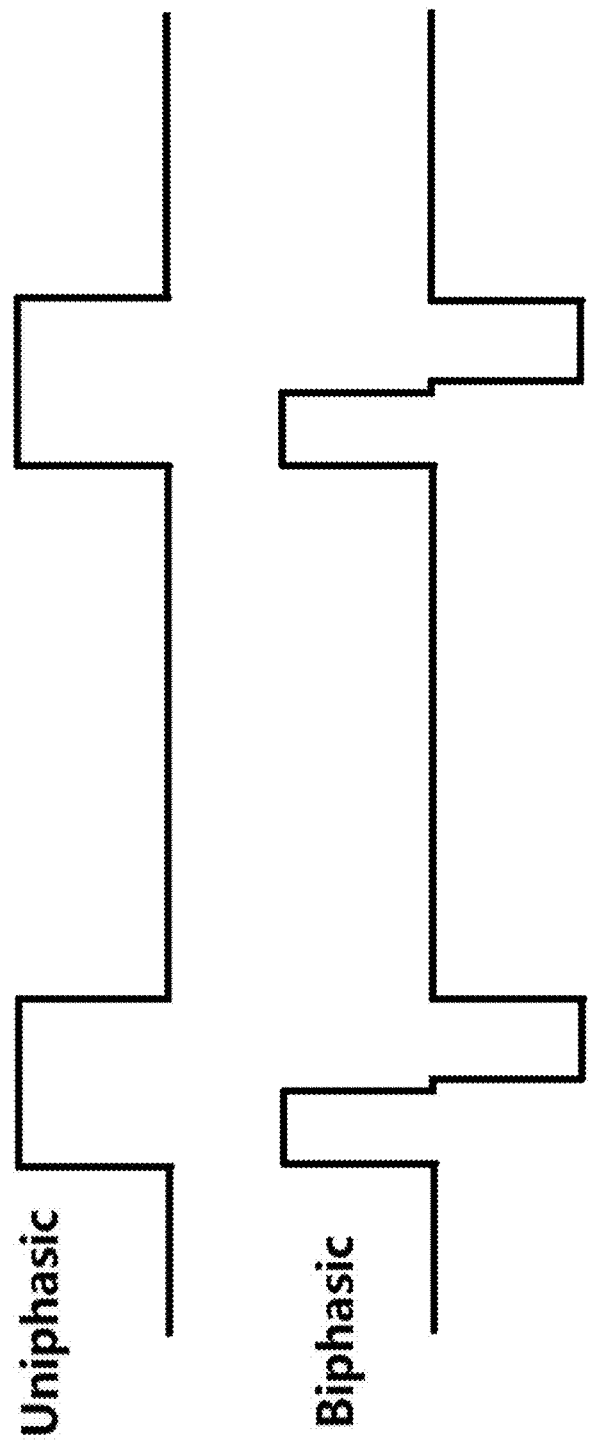
FIG. 22 shows the uniphasic and biphasic stimulus pulses, either current or voltage, in accordance with an embodiment of the invention.
Figure 23:
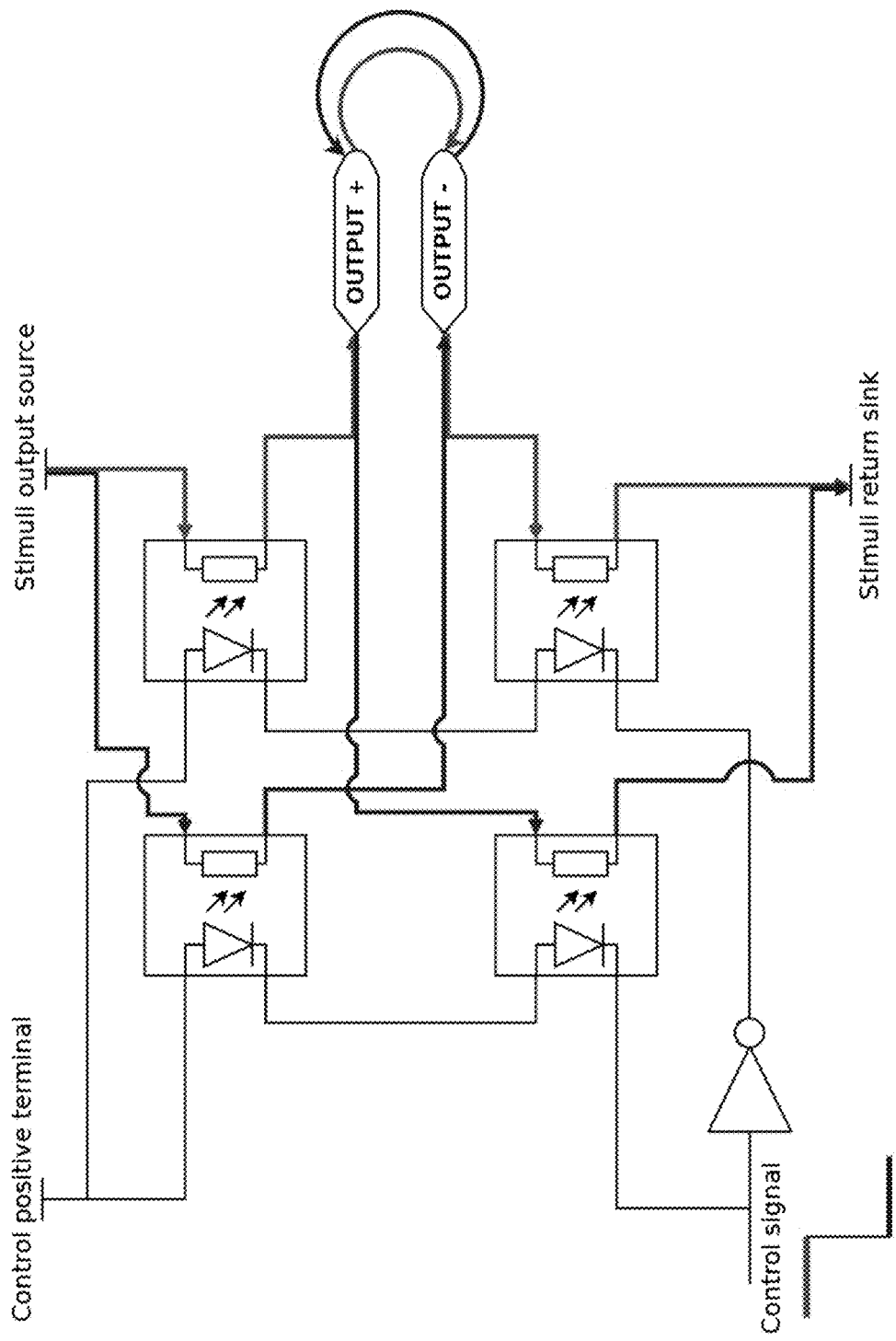
FIG. 23 is a schematic of the conceptual design for the uniphase/biphase pulses, in accordance with an embodiment of the invention.

The NeuroNet-VII System is the only system which supports both uniphasic and biphasic stimulation for electrical stimulation, shown in FIG. 22. The inventive circuit design uses a fast switching array chipset which provides very short delay phase switching of less than 5 usec for biphasic stimulation. The conceptual design of using switching array to implement uniphasic/biphasic stimulation is shown in FIG. 23.

Auditory Visual Stimulator

Figure 24:
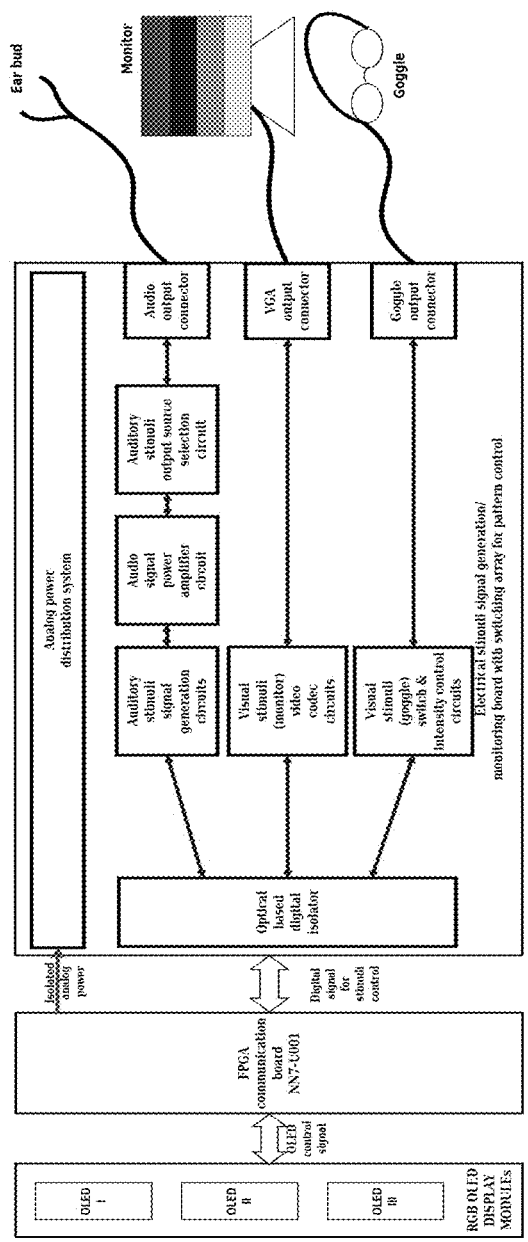
FIG. 24 shows the structure of the auditory and visual stimulator module, in accordance with an embodiment of the invention.

The Auditory/Visual Stimulator module supports output to ear buds for auditory stimulation, and output to either a VGA monitor or goggles for visual stimulation. The structure of the Auditory/Visual Stimulator module is shown in FIG. 24.

Full Color Complex Pattern Visual Stimulation with VGA Monitor

One method of providing visual stimulation is by a monitor driven through by a VGA full color range encoder chip. Patterns are predefined with different color, texture, intensity, and flashing frequency in the System user interface. This information then is sent through the USB communication network to the FPGA, where it is parsed and transferred to the encoder chip for display. The full color range stimulation with variety patterns and frequency makes the System of the present invention more capable for the complicated visual-related evoked potential signal monitoring than prior art systems.

Goggle with Various Block Patterns

Figure 25:
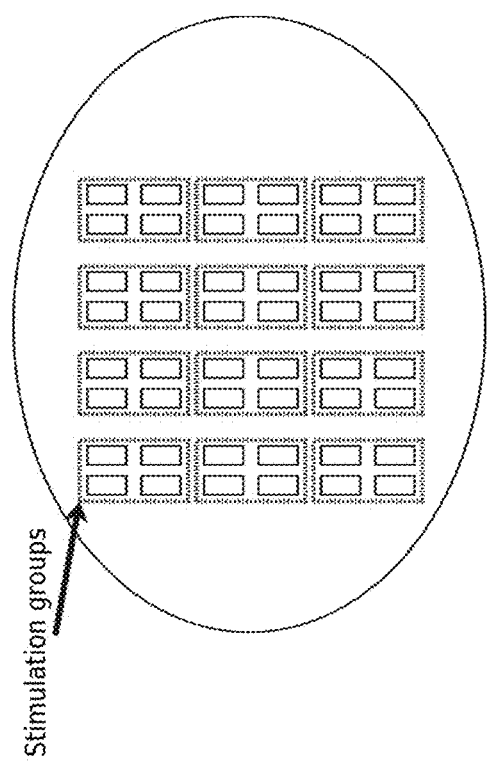
FIG. 25 is an illustration of the Goggle LED layout and stimulation groups, in accordance with an embodiment of the invention.

In prior art IONM systems, a stimulation goggle has a stimulation pattern which is a full flashing screen. The inventive System design implements stimulation patterns by grouping LEDs into a 3 by 4 matrix in each eye with each block having 2×2 LEDs, as shown in FIG. 25. This design allows the goggles to support various stimulation patterns provided to a patient during surgery.

System Isolation Architecture

Figure 26:
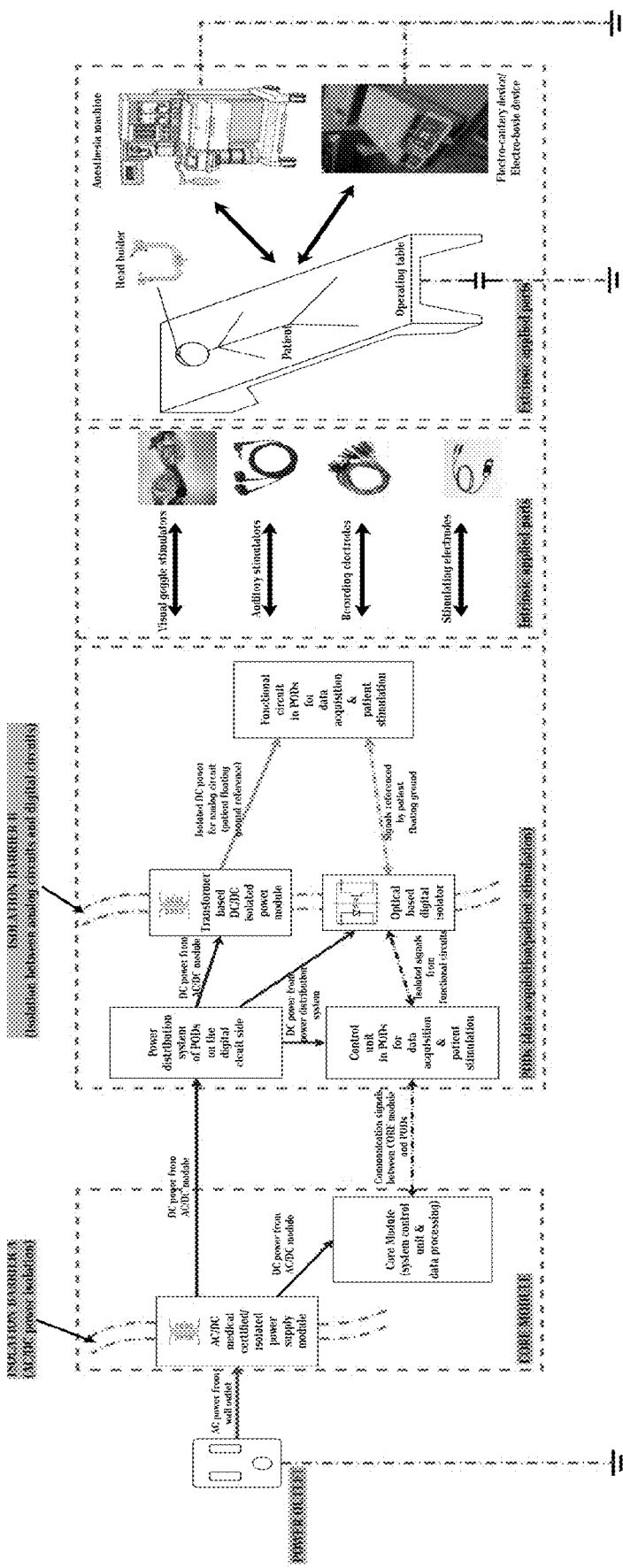
FIG. 26 is an assembly drawing showing the system isolation architecture, in accordance with an embodiment of the invention.

The NeuroNet VII system of the present invention has to be well isolated in order to isolate a patient from a current path from the patient to earth ground. Because this system includes both analog and digital electronic circuitry, the isolation barrier implemented in the System contains both analog and digital isolation. The first layer of isolation is power isolation obtained by utilizing a medical grade AC/DC power regulator. This power regulator enables medical grade current leakage from our system to the earth ground. The second layer of the isolation barrier consists of two parts: the first part is an isolated DC/DC power regulator which isolates the digital power supply from the analog power domain; and the second part is the control signal isolation chip which makes it possible for the analog circuits to be controlled by the digital control unit without providing a current path from the subject to the earth ground. FIG. 26 shows the System Isolation Architecture. This is the equivalent of having three layers of electrical isolation.

While the invention has been particularly shown and described with reference to embodiments described above, it will be understood by those skilled in the art that various alterations in form and detail may be made therein without departing from the spirit and scope of the invention, as defined by the appended claims.

The invention claimed is:

1. A modular NeuroNet-VII intraoperative neurophysiological monitoring (IONM) system for use during a surgical procedure on a patient, said system comprising:

axon architecture comprising a compute module, a plurality of neuron boards, and a plurality of axon cables; and at least three data acquisition functional modules which provide signal amplification, signal filtering, and analog to digital conversion of electronic signals prior to differencing, at least one electrical stimulation functional module, and at least one audio/visual (A/V) stimulation functional module, each functional module serially interconnected together in any order, each functional module containing one of said plurality of neuron boards, each of said plurality of neuron boards comprising (a) a field programmable gate array (FPGA) chip to control functioning of the functional module, (b) a system-designed USB hub structure comprised of a system-designed USB type C hub and a USB adapter/controller, (c) a module power distribution system, (d) an isolated power module, (e) a digital isolator, (f) a multiplexer circuit, and (g) a function board, wherein said plurality of neuron boards provides bidirectional communication between the serially connected functional modules, (b) manages power distribution to the functional modules, (c) manages data transmission of the functional modules, (d) provides system synchronization of the functional modules, and (e) controls data output from the functional modules, wherein the data acquisition module includes a pin/filter board comprised of a low pass filter with more than −60 dB suppression at 300 kHz and 0 dB at less than 3 kHz, said low pass filter comprised of an inductor-capacitor (LC)-based third order active electrosurgical suppression filter which provides low thermal noise frequency bandpass properties required for continued signal acquisition without saturation during use of an electrosurgery device, wherein said compute module comprises either a core module or comprises a portable laptop with a connected adapter module, said core module further comprised of a base board, a core board, a power supply and a speaker module, said adapter module further comprised of a base board, a power supply and a speaker module, wherein said compute module is configured to be a head, or first, module in the serially connected functional modules, wherein said compute module provides signal processing and computational processing, displays and stores data, provides for data communication with the serially connected functional modules, acquires and integrates data from other devices used during a surgical procedure, and connects to the internet through an ethernet connection or wirelessly, wherein each of said plurality of axon cables has a USB type C receptacle at each end, said USB type C receptacle configured to provide a connection interface to the USB type C hub contained in each neuron board downstream from a first serially connected functional module, and to a standard USB hub contained in the laptop, and to provide a power load and data communication between the base board and a first serially connected functional module, wherein only one of said plurality of axon cables runs from the base board of the NeuroNet-VII IONM system to an operating table, wherein the functional modules may be serially connected in any order with no requirement as to which functional module is serially connected last, wherein the system is configured to allow branching of the functional modules so that up to thirty-one functional modules may be serially connected, wherein the system-designed USB hub structure in each neuron board is configured so that the plurality of serially connected functional modules are recognized by the compute module as USB type C devices and the compute module recognizes where in the serial connection each of the functional modules is located and assigns each of the functional modules a specific identification.

2. The modular NeuroNet-VII IONM system of claim 1, wherein the core board is an artificial intelligent embedded core-enabled computer board, an embedded digital signal processing core, and an embedded micro-controller core, wherein the core board (a) receives data from the base board and the functional modules, (b) processes, displays and stores the data, (c) manages all computational processes, (d) provides an audio interface for a speaker module having an audio power amplifier (e) includes an ethernet port and (f) includes an embedded wireless module which allows for wireless communication so that the system may be controlled remotely and data may be shown to users.

3. The modular NeuroNet-VII IONM system of claim 2, wherein the hub structure of the compute module is configured to form up to seven cascading tiers of modules comprising the core board and up to five serially connected functional modules.

4. The modular NeuroNet-VII IONM system of claim 3, wherein the hub structure comprises seven tiers of modules comprised of Tier 1 through Tier 7, wherein the core board contains Tier 1 and Tier 2, said Tier 1 comprised of a USB root hub directly attached to a USB host controller in a CPU chip in the core module, said Tier 2 comprised of one USB type C hub which connects to the USB root hub in Tier 1, said USB type C hub in Tier 2 providing a port which connects to a second USB type C hub in an adjacent Tier 3 functional module I via an axon cable, said second USB type C hub connecting to a USB adapter contained in Tier 3 and providing a port which connects to a third USB type C hub in an adjacent Tier 4 functional module II via an axon cable, said third USB connecting to a USB adapter contained in Tier 4 and providing a port which connects to a fourth USB type C hub contained in an adjacent Tier 5 functional module III via an axon cable, said fourth USB type C hub connecting to a USB adapter container in Tier 5 and providing a port which connects to a fifth USB type C hub contained in an adjacent Tier 6 functional module IV via an axon cable, said fifth USB type C hub connecting to a USB adapter contained in Tier 6 and providing a port which connects to a USB adapter contained in an adjacent Tier 7 functional module V via an axon cable.

5. The modular NeuroNet-VII IONM system of claim 3, wherein the hub structure comprised of the portable laptop and the base board of the adapter module also is configured to form up to seven cascading tiers of modules, wherein Tier I comprises the laptop containing a USB root hub attached to a USB host controller in a CPU chip and Tier 2 comprises the base board, wherein because the serially connected functional modules cannot connect directly to a standard USB type C port of a conventional computer, the base board provides a connection interface, said interface comprised of a USB type C port to connect to the Tier 3 through Tier 7 serially connected functional modules via an axon cable and a standard USB type B port to connect to the standard USB type C port of the laptop.

6. The modular NeuroNet-VII IONM system of claim 5, wherein a switching circuit contained in each of the plurality of neuron boards in each of the functional modules is configured to detect whether an adjacent downstream functional module is plugged in to an adjacent functional module or is the last functional module in the serial connection, wherein when a functional module is determined not to be last in the serial connection, the switching circuit includes both the USB type C hub and the USB adapter in a circuit in that functional module, wherein when the switching circuit detects that a functional module is last in the serial connection, the USB type C hub in the functional module is switched out of the circuit so that only the USB adapter in the last functional module is active which ensures that only five functional modules are serially connected.

7. The modular NeuroNet-VII IONM system of claim 6, wherein the switching circuit in each neuron board is configured to detect power load and load current on a ground wire in each of the plurality of USB type C axon cables, wherein when one or more functional modules are serially connected downstream to a particular functional module, the power load and the load current of the axon cable and the ground wire is detected by the switching circuit and a detection signal is generated which is used to drive a selection signal on the multiplexer circuit on the neuron board, wherein the multiplexer circuit switches on a connection channel between the USB type C hub and the USB adapter, wherein the switching unit detects no power load or load current in a USB type C axon cable downstream from a functional module that is the last Tier 7 Functional Module V in the serial connection, which has no power load or load current going downstream, so that no detection signal is generated which ensures that only five functional modules are serially connected.

8. The modular NeuroNet-VII IONM system of claim 7, wherein the system further comprises application software which issues a warning to a user when a sixth serial module is serially connected, said warning alerting the user that the sixth serial module will not function, said application software also issuing a control signal to the switching circuit which functionally disconnects the sixth serial module from the serially connected Tiers 1 through 7.

9. The modular NeuroNet-VII IONM system of claim 1, wherein the base board provides data concatenation and provides system synchronization to each of the plurality of neuron boards contained in the functional modules, wherein the base board is an FPGA-based multimedia data acquisition board which is configured to acquire data from multiple sources in an operating room, said data comprising video, images, and data from an anesthesia monitor, wherein the data are encapsulated by the FPGA, sent to the core board, and then broadcast for viewing.

10. The modular NeuroNet-VII IONM system of claim 9, wherein the system synchronization comprises a synchronization protocol which synchronizes, within 63 μsecs, data acquired from a data acquisition functional module from each data sample and stimulus in order to provide near real-time operation and to ensure that all data are aligned for processing, said system synchronization protocol comprising a synchronization clock on the base board which provides a common synchronization signal to each of the plurality of neuron boards in the functional modules so that the base board and the functional modules are running under the same clock, wherein the system synchronization protocol comprises: (a) an Acquire Data command issued by a user, (b) the base board sends a USB system synchronization signal to each of the plurality of neuron boards in the functional modules, (c) each of the plurality of neuron boards in the functional modules receives the synchronization signal and sends a response back to the base board to indicate that the functional modules are ready for system synchronization, (d) the base board sends a digital logic pulse to each of the plurality of neuron boards in the functional modules, (e) each of the plurality of neuron boards in the functional modules detects the digital logic pulse, and (f) each of the plurality of neuron boards in the functional modules resets its internal counter and register so that that all of the functional modules start with a same initial time.

11. The modular NeuroNet-VII intraoperative neurophysiological monitoring system of claim 1, wherein each data acquisition functional module contains 24 electrodes and the system assigns electrodes of the data acquisition functional module that is first in the serial connection numbers 1 through 24; assigns electrodes of the data acquisition functional module that is second in the serial connection numbers 25 through 48; and assigns electrodes of the data acquisition functional module that is third in the serial connection numbers 49 through 72, wherein one of the at least three data acquisition functional modules need not be the first functional module in the serial connection and the three data acquisition functional modules need not be adjacent to one another.

12. The modular NeuroNet-VII IONM system of claim 1, wherein each of the at least three data acquisition modules further comprises a pin/filter board, twenty-four channels of amplification with DC drift suppression which supports acquiring data from its twenty-four electrodes, feedback common mode noise suppression signals, differencing between pairs of electrode signals after analog to digital (A/D) conversion, said A/D conversion referred to as digitization, and an organic light-emitting diode (OLED) display board, said data acquisition module capable of acquiring neurophysiological data ranging from 0.1 µvolt to 1000 µvolts in amplitude.

13. The modular NeuroNet-VII IONM system of claim 12, wherein the digitization is implemented by an analog-to-digital convertor, said analog-to-digital convertor configured to difference different pairs of electrodes from any one of the data acquisition modules to increase ways of presenting data.

14. The modular NeuroNet-VII intraoperative neurophysiological monitoring system of claim 13, wherein each of the data acquisition modules provides a stimulus artifact blanking and trace restore function controlled by the FPGA chip on its neuron board comprised of an N-channel MOSFET controllable switch which is used to provide a path for a signal to an analog ground, wherein a logic 1 control closes the MOSFET switch and an input terminal of an amplifier is pulled to analog ground, wherein the stimulus artifact blanking and trace restore function allows for data to be acquired without containing contaminating stimulus artifacts and allows for electrical stimulation to be applied adjacent to recording electrodes so that signals are capable of being recorded through the recording electrodes immediately after completion of the electrical stimulation.

15. The modular NeuroNet-VII IONM system of claim 12, wherein the feedback common mode noise suppression signals comprises utilizing a feedback signal to a patient of a noise component of signals that are being measured, said feedback signal capable of balancing out common mode noise of the twenty-four electrodes.

16. The modular NeuroNet-VII IONM system of claim 12, wherein three color OLED display screens are utilized in each of the at least three data acquisition modules to display data from each of the at least three data acquisition modules, module number, and identification of the twenty-four electrodes.

17. The modular NeuroNet-VII IONM system of claim 1, wherein the at least one electrical stimulator module further comprises a stimulator pin board, an extender module board, and three color OLED display screens to display identification of the electrical stimulator module.

18. The modular NeuroNet-VII intraoperative neurophysiological monitoring system of claim 17, wherein the at least one electrical stimulation module includes a plurality of electrical stimulators to produce a variety of train patterns for stimuli, said variety of train patterns capable of being synchronized to provide simultaneous acquisition of multi-modality electrical evoked potentials, wherein control of the variety of train pattern stimuli is provided by the FPGA chip on the neuron board contained in the electrical stimulation module, wherein the electrical stimulation module provides both constant current mode stimulation and constant voltage mode stimulation, both capable of being used interchangeably for electrical stimulation, wherein the constant current mode stimulation and constant voltage mode stimulation support uniphasic and biphasic electrical stimulation, said uniphasic and biphasic electrical stimulation capable of being used interchangeably for electrical stimulation.

19. The modular NeuroNet-VII IONM system of claim 1, wherein the at least one audio/visual stimulator module further comprises an audio/visual stimulation board, three color OLED display screens to display identification of the audio/visual stimulator module, output to ear buds for auditory stimulation, and output to a video graphic array (VGA) monitor or goggles for visual stimulation, wherein visual stimulation by the VGA monitor is driven through a VGA full color range encoder chip, wherein patterns are predefined with different colors, textures, intensities, and flashing frequencies to produce a variety of patterns and frequencies, wherein the full color range visual stimulation with the variety of patterns and frequencies allows the IONM system to produce complicated visual-related evoked potential signal monitoring, wherein control of the variety of patterns and frequencies is provided by the FPGA chip on each of the plurality of neuron boards.

* * * * *